United States Patent [19]

Lau et al.

[11] Patent Number: 5,683,989

[45] Date of Patent: Nov. 4, 1997

[54] TREATMENT OF ISCHEMIAS BY ADMINISTRATION OF 2,N⁶-SUBSTITUTED ADENOSINES

[75] Inventors: Jesper Lau, Farum; Lars Jacob Stray Knutsen, Vedbæk; Malcolm Sheardown, Smørum; Anker Jon Hansen, Charlottenlund, all of Denmark

[73] Assignee: Novo Nordisk A/S, Bagsvaerd, Denmark

[21] Appl. No.: 504,811

[22] Filed: Jul. 20, 1995

Related U.S. Application Data

[63] Continuation of Ser. No. 169,097, Dec. 17, 1993, Pat. No. 5,484,774.

[51] Int. Cl.⁶ .................. A61K 31/70; C07H 19/167
[52] U.S. Cl. .............. 514/46; 536/27.61; 536/27.62; 536/27.63; 536/27.7
[58] Field of Search .............. 514/46; 536/27.61, 536/27.62, 27.63, 27.7

[56] References Cited

U.S. PATENT DOCUMENTS

| | | | |
|---|---|---|---|
| 3,590,029 | 6/1971 | Koch et al. | 536/27.61 |
| 3,901,876 | 8/1975 | Vorbrüggen et al. | 536/27.62 |
| 4,341,769 | 7/1982 | Marumoto et al. | 514/46 |
| 4,600,707 | 7/1986 | Patt | 514/46 |
| 4,657,897 | 4/1987 | Bristol et al. | 514/47 |
| 4,657,898 | 4/1987 | Bristol et al. | 514/47 |
| 4,704,381 | 11/1987 | Schaumann et al. | 514/46 |
| 5,043,325 | 8/1991 | Olsson et al. | 514/46 |
| 5,484,774 | 1/1996 | Lau et al. | 514/46 |

FOREIGN PATENT DOCUMENTS

| | | |
|---|---|---|
| 0423777 | 4/1991 | European Pat. Off. . |
| 8504482 | 11/1985 | WIPO . |
| 9205177 | 4/1992 | WIPO . |

OTHER PUBLICATIONS

Olsson et al. "N⁶-Substituted N-Alkyladenosine-5'-uronamides: Bifunctional Ligands Having Recognition Groups for A1 and A2 Adenosine Receptors," *J. Med. Chem.*, 29(9), 1683–1689 (1986).

Cadogan et al., "On the Formation of Benzenediazonium Chloride in Gomberg-Hey Type Reactions of Diazonium Salts with Bromotrichloromethane, Carbon Tetrachloride, and Chloroform. The Solution of a Long-standing Mechanistic Puzzle," *J. Chem. Soc. Chem. Comm.*, 1976, 851–852.

Vorbrüggen et al., "Einfach neue Synthese von N⁶-Substituierten Adenosinen und Adeninen sowie ihrer 2-Amino-and 2-Hydroxyderivate," *Liebigs Ann. Chem.*, 1976, 745–761.

Nair et al.(I), "Utility of Purinyl Radicals in the Synthesis of Base-Modified Nucleosides and Alkylpurines: 6-Amino Group Replacement by H, CL, Br, and I," *J. Organic Chem.*, 45(20), 3936–3974 (1980).

Nair et al. (II), "Modification of Nucleic Acid Bases via Radical Intermediates: Synthesis of Dihalogenated Purine Nucleosides", *Synthesis*, 1982, 832–834.

Koster et al., "Some Improvements in the Synthesis of DNA of Biological Interest," *Nucleic Acids Research, Symposium Series No. 7*, IRL Press Ltd., 1980, London, U.K., pp. 39–60.

Goodman, "Chemical Syntheses and Transformations of Nucleosides," Ch. 2 in *Basic Principles in Nucleic Acid Chemistry*, Academic Press, New York, 1974, pp. 94–208, only pp. 153–154 and subsequent pages with reference citations supplied.

*Primary Examiner*—Gary L. Kunz
*Assistant Examiner*—L. Eric Crane
*Attorney, Agent, or Firm*—Steve T. Zelson, Esq.; Elias J. Lambiris, Esq.

[57] ABSTRACT

The present invention relates to compounds of formula I

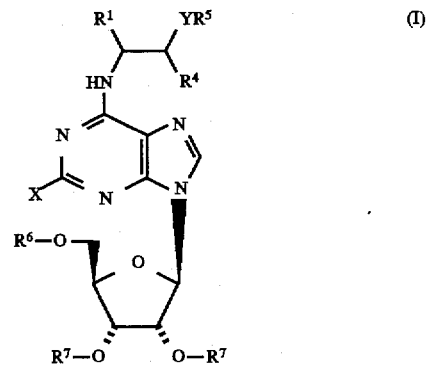

wherein

X is amino, $C_{1-6}$-alkylamino, di-$C_{1-6}$-alkylamino;

$R^1$ is H, straight or branched $C_{1-6}$-alkyl or trifluoromethyl; $R^4$ is H or straight or branched $C_{1-6}$-alkyl; or $R^1$ and $R^4$ together form a cyclobutyl, cyclopentyl or cyclohexyl ring;

Y is O, S, $SO_2$, N—H or N-alkyl;

$R^5$ is selected from optionally substituted heterocycles;

$R^6$ is hydrogen, benzoyl or $C_{1-6}$-alkanoyl and $R^7$ is hydrogen, benzoyl or $C_{1-6}$-alkanoyl; or a pharmaceutically acceptable salt thereof.

The compounds have been found useful for treating central nervous system and cardiovascular ailments.

32 Claims, No Drawings

TREATMENT OF ISCHEMIAS BY ADMINISTRATION OF 2,N⁶-SUBSTITUTED ADENOSINES

This application is a continuation of U.S. Ser. No. 08/169,097, filed Dec. 17, 1993, now U.S. Pat. No. 5,484,774, the contents of which are herein incorporated by reference.

The present invention relates to therapeutically active N-substituted adenosine derivatives which are substituted at the purine 2-position and pharmaceutically acceptable addition salts thereof, processes for their preparation as well as methods for alleviation of diseases treatable via adenosine receptors, to compounds for use in such a method and to pharmaceutical compositions containing the said compounds.

BACKGROUND OF THE INVENTION

Adenosine is a naturally occurring purine nucleoside, from which is derived a range of agonists at adenosine receptors having considerable potential in the treatment of human disease (Life Sciences, 1991, 49, 1435–1453; Journal of Medicinal Chemistry, 1992, 35, 407–422; Annual Reports in Medicinal Chemistry, 1993, 28, 295–304).

Adenosine has been shown to have a number of significant effects on the mammalian central nervous system (CNS) (Annual Reports in Medicinal Chemistry, 1988, 23, 39–48; Adenosine in the Nervous System, T. W. Stone, Ed., Academic Press Ltd., London 1991) especially under conditions of neuronal stress where the compound appears to act as an endogenous neuroprotectant (Progress in Neurobiology, 1988, 31, 85–108, Trends in Pharmacological Sciences, 1992, 11,439–445). For example, the concentration of adenosine has been demonstrated to rise greatly in certain brain regions following epileptic seizures or conditions of neuronal ischaemia/anoxia (Brain Research, 1990, 516, 248–256).

It has been established for some years now that centrally acting adenosine receptor agonists or compounds which increase extracellular adenosine levels can exhibit what is termed neuromodulator activity (Trends in Neurosciences, 1984, 164–168). Such substances influence the release of neurotransmitters in regions of the central nervous system (Annual Review of Neuroscience, 1985, 8, 103–124; Trends in Neurosciences, 1984, 164–168), with particular inhibitory effects on the release of the excitatory amino acid glutamic acid (glutamate) in the CNS (Nature, 1985, 316, 148–150) especially under ischaemic conditions (Journal of Neurochemistry, 1992, 58, 1683–1690).

There are therefore several CNS ailments for which this adenosine receptor mediated neuromodulator activity could be of clear therapeutic benefit. Examples of these would include the treatment of convulsive disorders (European Journal of Pharmacology, 1991, 195, 261–265; Journal of Pharmacology and Experimental Therapeutics, 1982, 220, 70–76; European Journal of Pharmacology, 1993, 242, 221–228), prevention of neurodegeneration under conditions of brain anoxia/ischaemia (Neuroscience Letters, 1987, 83, 287–293; Stroke, 1988, 19, 1133–1139; Neuroscience, 1989, 30, 451–462; Pharmacology of Cerebral Ischaemia 1990, (Kriegelstein, J. and Oberpichler, H., Eds.; Wissenschaftliche Verlagsgesellschaft mbH: Stuttgart, 1990, pp 439–448; Trends in Pharmacological Sciences 1992, 11, 439–445) or the use of a purinergic agent in the treatment of pain (European Journal of Pharmacology, 1989, 162, 365–369; Neuroscience Letters, 1991, 121, 267–270).

Adenosine receptors represent a subclass ($P_1$) of the group of purine nucleotide and nucleoside receptors known as purinoreceptors. This subclass has been further classified into two distinct receptor types which have become known as $A_1$ and $A_2$. Extensive research has been carried out in a quest to identify selective ligands at these sites. Selective ligands exist for $A_1$ and $A_2$ adenosine receptors and the structure-activity relationships of the various reference ligands have been reviewed (Biochemical Pharmacology, 1986, 35, 2467–2481; Comprehensive Medicinal Chemistry, Volume 3, (Hansch, C., Sammes, P. G. and Taylor, J. B., Eds., Pergamon Press PLC: 1990, pp 601–642). Among the known adenosine receptor agonists most selective for the $A_1$ receptor over the $A_2$ receptor are the examples where the adenine nucleus is substituted with a cycloalkyl group on the amino function, for example N-cyclopentyladenosine (CPA) and N-cyclohexyladenosine (CHA) (Journal of Medicinal Chemistry, 1985, 28, 1383–1384) or 2-chloro-N-cyclopentyladenosine (CCPA) (Naunyn-Schmiedeberg's Arch. Pharmacol. 1988, 337, 687–689).

Various examples of N-heteroarylalkyl substituted $A_1$ selective adenosine analogues have been reported in the literature. It should be noted that some of these are named as N-6 or $N^6$-substituted adenosine derivatives, but this is equivalent to the American Chemical Society suggested nomenclature where compounds substituted on adenosine's 6-amino position are referred to as N-substituted adenosine derivatives.

There is evidence for further subdivision of adenosine receptors into the subtypes $A_{2a}$, $A_{2b}$ (of high and low affinity), $A_3$ and $A_4$. The latest status of these subtypes has been reviewed (Journal of Biological Chemistry, 1992, 267, 6451–6454; Drug Development Research, 1993, 28, 207–213; Trends in Pharmacological Sciences 1993, 290–291 ). The $A_3$ receptor (Proceedings of the National Academy of Sciences of the USA, 1992, 89, 7432–7436) appears to be responsible for some of the cardiovascular effects of reference ligands (British Journal of Pharmacology, 1993, 109, 3–5).

The synthesis and pharmacological properties of N-thienylalkyl and N-pyridylalkyl adenosine derivatives has been published in the scientific literature (e.g. Nucleosides and Nucleotides, 1992, 11, 1077–1088; Nucleosides and Nucleotides, 1991, 10, 1563–1572; Canadian Journal of Pharmacology, 1986, 333, 313–322). Furthermore, 2-substituted N-piperidinyladenosine derivatives have been described recently (Bioorganic and Medicinal Chemistry Letters, 1993, 3, 2661–2666).

Certain N-imidazolylalkyl and N-indolylalkyl adenosine derivatives have also been described (Life Sciences, 1987, 41, 2295–3202; Justus Liebigs Annalen der Chemie 1976, 4, 745–761; Chemical & Pharmaceutical Bulletin, 1974, 22, 1410–13, Biochemical Pharmacology, 1974, 23, 2883–2889).

Various studies of the 6-amino subregion of adenosines which include N-heteroarylalkyl substituents have been published (Journal of Medicinal Chemistry 1986, 29, 989–996; Naunyn-Schmiedeberg's Archives of Pharmacology, 1986, 333, 313–322; Biochemical Pharmacology, 1986, 35, 2467–2481).

Examples of modified adenosine derivatives containing a range of N-heteroarylalkyl substituents have been claimed in several patents and patent applications. For example EP 0 232 813 A2 includes N-heteroarylcycloalkylmethyl adenosines which are apparently useful as analgesics, antipsychotics, sedatives, antihypertensives and antianginals.

U.S. Pat No. 4,600,707 discloses N-benzothienyl adenosines and the corresponding N-oxide and S-dioxides as antipsychotics.

In WO 8504882 N-heteroarylethyl adenosines are claimed as cardiac vasodilators. Some similar analogues containing N-heteroarylalkyl adenosine compounds are included in Ger. Offen. DE 2147314, Ger. Offen. DE 2139107, EP 0 423 776 A2, EP 0 423 777 A2, U.S. Pat No. 4,340,730 and U.S. Pat. No. 1,164,580 without any mention being made of their potential pharmacological effects on the CNS.

PCT-publication WO 9205177 and U.S. Pat. No. 3,901,876 discloses N-substituted adenosine derivatives with hypotensive properties, none of them being further substituted at the purine 2-position.

Utility of adenosine receptor agonists as cerebral neuroprotectants is claimed in the following patents and patent publications: WO 90/05526, EP 0490818A1, U.S. Pat. No. 5,187,162, EP 526866A1, U.S. Pat. No. 5,219,839, WO 93/08206, WO 93/23417 and WO 93/23418.

The present invention relates to new adenosine analogues having potent binding in vitro to the adenosine $A_1$ receptor and at the same time showing selectivity for $A_1$ receptor binding in vitro over that of the $A_2$ receptor subtype (for method description, see European Journal of Pharmacology, 1993, 242, 221–228). In addition, the compounds contained in this invention have a relatively high lipophilicity, especially when compared to adenosine analogues which are not substituted on the 6-amino group or at the purine 2-position. This latter property makes these compounds suitable for passage across the blood brain barrier, and supports the suggestion that the compounds may be candidate drugs for the CNS and other ailments mentioned within this invention.

The possibility that some of the compounds may be substrates for nucleoside-specific active transport systems across the blood brain barrier is, however, not excluded. These useful properties support the suggestion that the compounds may be candidate drugs for the CNS ailments mentioned above in humans. There are however instances where it has been demonstrated that co-administration of a peripherally active adenosine receptor antagonist can lower the expected dose related side effects on the cardiovascular system when an adenosine agonist is used as a neuroprotectant in animal models (Journal of Molecular Neuroscience, 1990, 2, 53–59). This method of lowering potential side-effects is also applicable during the therapeutic use of the adenosine receptor agonists covered by the present invention.

The invention also covers the potential prodrugs of the adenosine derivatives described above. Adenosine sugar moiety esters which can find utility as prodrugs are exemplified in this patent.

The compounds of the invention are purine derivatives of formula (I), or a pharmaceutically acceptable salt thereof:

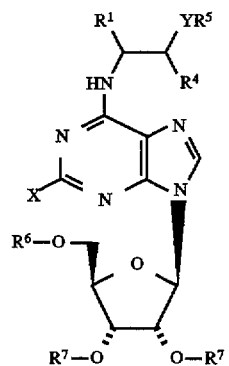

wherein
X is halogen, amino, trifluoromethyl, $C_{1-6}$-alkyl, $C_{1-6}$-alkoxy, $C_{1-6}$-alkylthio, cyano, $C_{1-6}$-alkylamino or di-$C_{1-6}$-alkylamino;

$R^1$ is H or straight or branched $C_{1-6}$-alkyl or trifluoromethyl;

$R^4$ is H or straight or branched $C_{1-6}$-alkyl;

or $R^1$ and $R^4$ together form a cyclobutyl, cyclopentyl or cyclohexyl ring;

Y is O, S, SO$_2$, N—H or N-alkyl;

$R^5$ is a group of formula (XI) or (XII):

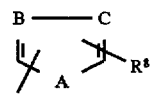

or

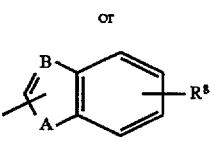

wherein A is —NH—, —O— or —S—;
B is —CH— or —N—;
C is —CH— or —N—;
which may be optionally substituted with $R^8$ which is H, phenyl, $C_{1-6}$-alkyl, tri-fluoromethyl, amino, hydroxy, $C_{1-6}$-alkoxy, cyano or halogen;

$R^6$ is hydrogen, benzoyl or $C_{1-6}$-alkanoyl and
$R^7$ is hydrogen, benzoyl or $C_{1-6}$-alkanoyl.

In certain examples, the group

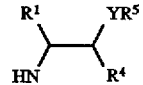

can contain one or more asymmetric carbon atoms in addition to those asymmetric centres already present in the ribose moiety of these adenosine agonists. The invention includes all resulting diastereoisomers and mixtures thereof.

The compounds according to the invention includes various salts which can be considered physiologically acceptable. These include addition salts derived from inorganic or organic acids, for example, acetates, fumarates, glutarates, glutaconates, hydrochlorides, lactates, maleates, methanesulphonates, phosphates, salicylates, succinates, sulphates, sulphamates, tartrates and para-toluenesulphonates. In some cases, solvates of either the free nucleosides or the acid addition salts can be isolated and these solvates may, for example, be hydrates or alcoholates.

Compounds according to the invention are for instance:

[1S,trans]-N-[2-[(2-Benzothiazolyl)thio]cyclobutyl]-2-chloroadenosine,

[1R,trans]-N-[2-[(2-Benzothiazolyl)thio]cyclobutyl]-2-chloroadenosine,

[1S,cis]-N-[2-[(2-Benzothiazolyl)thio]cyclobutyl]-2-chloroadenosine,

[1R,cis]-N-[2-[(2-Benzothiazolyl)thio]cyclobutyl]-2-chloroadenosine,

[1S,trans]-N-[2-[(2-Benzothiazolyl)thio]cyclohexyl]-2-chloroadenosine,

[1R,trans]-N-[2-[(2-Benzothiazolyl)thio]cyclohexyl]-2-chloroadenosine,

[1S,cis]-N-[2-[(2-Benzothiazolyl)thio]cyclohexyl]-2-chloroadenosine,

[1R,cis]-N-[2-[(2-Benzothiazolyl)thio]cyclohexyl]-2-chloroadenosine,

N-[(R)-1-(2-Benzothiazolyl)thio-2-propyl]-2-methoxyadenosine,

N-[(R)-1-(2-Benzothiazolyl)oxy-2-propyl]-2-chloroadenosine or

2-Chloro-N-[(R)-1-(6-hydroxy-2-benzothiazolyl)thio-2-propyl]adenosine.

Compounds of formula (I), which act as adenosine receptor agonists, are expected from observations in animal models to be useful in the treatment of central nervous system conditions such as anxiety, neuronal ischaemia/anoxia, convulsive disorders (f. inst. epilepsy) and neurodegeneration (including Parkinson's disease) in humans. This includes treating disorders where the blood flow to regions of the brain is interrupted, for example during traumatic head injury, cardiac arrest and stroke.

Further, the compounds of formula (I) are expected to be useful as analgesic agents, in lowering plasma free fatty acid levels or as cardiovascular agents, e.g. for the treatment of myocardial ischaemia.

The invention also relates to methods of preparing the above mentioned compounds. These methods comprise:

Method A

A compound of formula (I) may be prepared by reacting a substance of formula (II), wherein L represents a leaving group such as a halogen atom (e.g. a chlorine or bromine atom) or a trimethylsilyloxy group, $R^2$ and $R^3$ are the same or different and represent hydrogen or a protecting group such as benzoyl-, p-toluoyl-, $C_{1-6}$-alkanoyl- (e.g. acetyl-), a 2,3-O-(1-methyl)- ethylidene group or a substituted silyl group (e.g. a trimethylsilyl or t-butyldimethylsilyl group) (for descriptions see Nucleic Acid Chemistry, Townsend L. B. and Tipson, R. S., eds., John Wiley and Sons Inc., 1986, 3. and earlier volumes) with an amine derivative of general formula (III), synthesised according to methods known in the art (see for example WO 93/08206 and WO 93/23418)

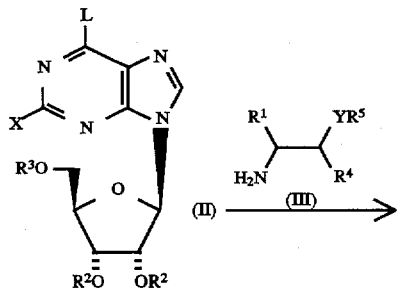

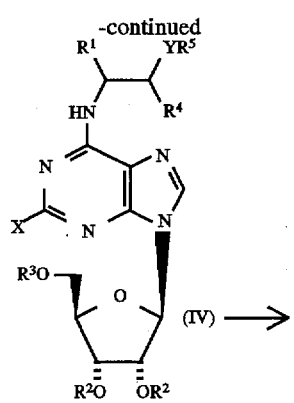

giving the compound of formula (IV) as the reaction product. In cases where $R^2$ and $R^3$ are not hydrogen an additional step will be required to remove protecting groups from a compound of formula (IV); in cases where the groups $R^2$ and $R^3$ are for example $C_{1-6}$-alkanoyl- or benzoyl-, suitable conditions for deprotection include methanolic ammonia, an alkali metal carbonate in methanol, an alkali metal alkoxide in the corresponding alcohol. Where the protecting groups are for example alkylsilicon or arylsilicon derivatives, suitable deprotection methods include for example treatment with tetraalkylammonium fluorides or aqueous hydrolysis in the presence of acid or base.

Method B

A compound of formula (I) wherein X represents —NH—$R^9$, S—$R^9$ or —O—$R^9$, where $R^9$ is $C_{1-6}$-alkyl may be prepared by reacting a substance of general formula (V)

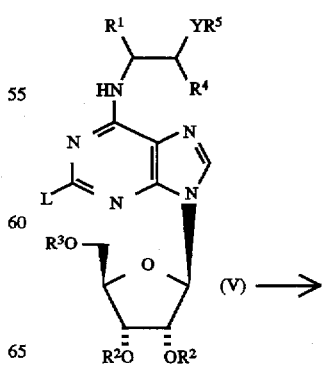

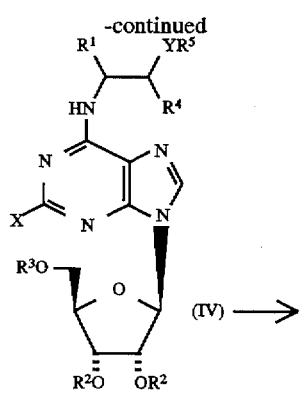

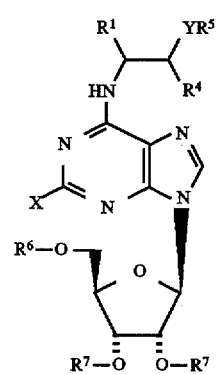

(where L is a leaving group as defined in method (A)) with a nucleophile, for example $C_{1-6}$-alkylamino (optionally in the presence of a suitable base) or with the anion ($C_{1-6}$-alkoxide or $C_{1-6}$-thioalkoxide) to afford (IV). In cases where $R^2$ and $R^3$ are hydrogen, a compound of formula (I) can be obtained directly. However, in cases where $R^2$ and $R^3$ are not hydrogen an additional step will be involved to remove protecting groups such as $C_{1-6}$-alkanoyl- or benzoyl- from a compound of formula (IV); examples of conditions for removal of protecting groups are given in process (A). In some reactions involving nucleophilic substitution of a compound of formula (V) with the anion ($C_{1-6}$-alkoxide or $C_{1-6}$-thioalkoxide), where $R^2$ and $R^3$ are for example $C_{1-6}$-alkanoyl- or benzoyl- partial or full deprotection may take place. In cases where only partial deprotection has taken place, deprotection can be completed under conditions exemplified in method (A).

Method C

A compound of formula (I) may be prepared by reacting a substance of the general formula (VI) (where B represents

or L as defined previously) with a diazotising agent (such as, for example, 3-methylbutyl nitrite) to form a diazo-intermediate which can be reacted further with a variety of substrates (for example chloroform, tetrachloroethane, trimethylsilylchloride, bromoform or fluoroboric acid) as exemplified below in order to introduce the group —X into a compound of formula (VII).

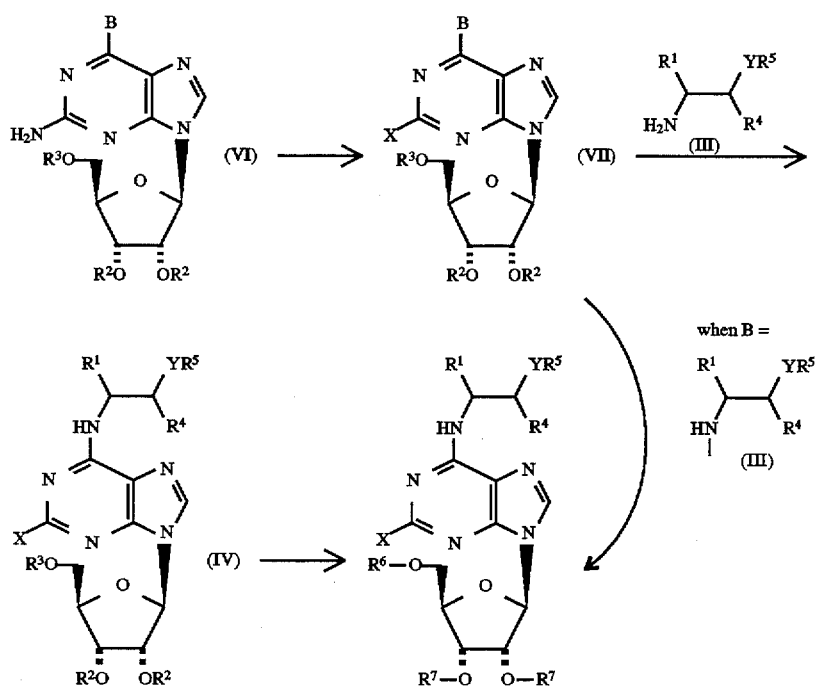

In the case where B represents a leaving group L, a further displacement reaction with for example a compound of formula (III) will be required in order to obtain a compound of formula (IV). In cases where the groups $R^2$ and $R^3$ are not hydrogen, or not all hydrogen, another step will be required to remove protecting groups from a compound of formula (IV); conditions for removing protecting groups are described in method A.

Compounds of formula (I) in which $R^6$ and $R^7$ are $C_{1-6}$-alkanoyl- or benzoyl-, may be prepared according to methods A–C as compounds of formula (IV) and (VII) in which $R^2$ and $R^3$ are represented by $C_{1-6}$-alkanoyl- or benzoyl-. In cases where $R^2$ and $R^3$ are different from $R^6$ and $R^7$, $R^2$ and $R^3$ can be replaced with hydrogen, $C_{1-6}$-alkanoyl- or benzoyl- according to methods known in the art.

Methods for assessing adenosine receptor binding in vitro have been reviewed [Adenosine Receptors, (Cooper, D. M. F. and Londos, C., eds.) Alan R. Liss, Inc., New York, 1988, 43–62].

Evaluation of these compounds in established animal models has indicated that the compounds according to the invention possess desirable central nervous system properties. For example, they act as anticonvulsant agents, are effective in animal paradigms of pain, and show cerebroprotective effects in laboratory test animals subjected to simulated cerebral ischaemia. In addition, the compounds may have efficacy as neuroprotective agents in cases of cerebral oedema and traumatic head injury, and as protectants in myocardial ischaemia.

Evaluation of in vitro binding to adenosine $A_1$ and $A_2$ receptors

The affinity of the novel compounds described in this invention for the adenosine $A_1$ receptor was determined essentially as described in the literature using [$^3$H]-(R)-PIA [N-(R)-(1-phenyl-2-propyl)adenosine] as a radioligand (Naunyn-Schmiedeberg's Archives of Pharmacology, 1980, 313, 179–187). Affinity for the $A_2$ receptor was measured using the radioligand [$^3$H]-CGS 21680 (European Journal of Pharmacology, 1989, 168, 243–246), and the values for representative compounds (single determinations only) are given in the table below. In vitro receptor binding values obtained for the reference standards CPA and (R)-PIA are included for comparison. The methods used are described fully in European Journal of Pharmacology, 1993, 242, 221–228.

DMCM INDUCED SEIZURES IN MICE I.P. 30 min

DMCM (methyl 6,7-dimethoxy-4-ethyl-β-carboline-3-carboxylate) is an inverse agonist at the benzodiazepine receptor, presumably producing seizures by decreasing the potency of inhibition of the GABA receptor/benzodiazepine receptor/chloride ionophore complex.

METHODS 18 mg/kg of DMCM dissolved in 0.02N HCl (1 mg/ml) is administered i.p. in a volume of 300 μl to male NMRI mice weighing 20±2 g. This induces two different responses: a) some animals manifest a brief loss of righting reflexes or take up an upright position in which they have a mild short clonus of the upper extremities, b) other animals manifest intense clonic and tonic convulsions of all extremities often followed by death. DMCM is administered 30 min after an intraperitoneal injection of a test compound. The latency time for the presence of intense clonic and tonic convulsions and death is noted until 15 min after administration of DMCM. At least 5 doses of each test compound are tested with 8 mice per dose. This method is described in more detail in European Journal of Pharmacology, 1993, 242, 221–228.

Test results obtained by testing compounds of the invention are presented in table I.

TABLE I

| Adenosine agonist tested (Example No.) | $A_1$ receptor binding ($K_i$, nM) | $A_2$ receptor binding ($K_i$, nM) | Ratio $A_2/A_1$ |
| --- | --- | --- | --- |
| 13 | 3.4 | 2570 | 756 |
| 23 | 4.5 | 170 | 38 |
| 15 | 7 | 950 | 136 |
| 3 | 9 | 990 | 110 |
| 22 | 10 | 1000 | 100 |
| 27 | 14 | 4970 | 355 |
| CPA | 1.2 | 192 | 160 |
| (R)-PIA | 1.9 | 116 | 61 |

The compounds of the invention, together with a conventional adjuvant, carrier, or diluent, and if desired in the form of a pharmaceutically acceptable acid addition salt thereof, may be placed into the form of pharmaceutical compositions and unit dosages thereof, and in such form may be employed as solids, such as tablets of filled capsules, or liquids, such as solutions, suspensions, emulsions, elixirs, or capsules filled with the same, all for oral use, in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective amount of the adenosine receptor agonist commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparation, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 0.05–100 mg in a pharmaceutically acceptable carrier per unit dosage.

The dosage of the compounds according to this invention is 0.1–300 mg/day, preferably 10–100 mg/day, when administered to patients, e.g. humans, as a drug.

A typical tablet which may be prepared by conventional tabletting techniques contains:

| | |
|---|---|
| Active compound | 5.0 mg |
| Lactosum | 67.0 mg Ph. Eur. |
| Avicel ™ | 31.4 mg |
| Amberlite ™IRP 88 | 1.0 mg |
| Magnesii stearas | 0.25 mg Ph. Eur. |

As a result of their activity against pain or convulsive disorders and prevention of neurodegeneration under conditions of anoxia/ischaemia the compounds of the invention are extremely useful in the treatment of related symptoms in mammals, when administered in an amount effective for agonist activity of compounds of the invention. The compounds of the invention may accordingly be administered to a subject, e.g., a living animal body, including a human, in need of adenosine receptor agonist, and if desired in the form of a pharmaceutically acceptable acid addition salt thereof (such as the hydrobromide, hydrochloride, or sulphate, in any event prepared in the usual or conventional manner, e.g., evaporation to dryness of the free base in solution together with the acid), ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount of adenosine receptor agonist, and in any event an amount which is effective for the treatment of anoxia, traumatic injury, ischaemia, migraine or other pain symptoms, epilepsy, or neurodegenerative diseases owing to their adenosine receptor agonist activity. Suitable dosage ranges are 1–200 milligrams daily, 10–100 milligrams daily, and especially 5–25 milligrams daily, depending as usual upon the exact mode of administration, form in which administered, the indication toward which the administration is directed, the subject involved and the body weight of the subject involved, and the preference and experience of the physician or veterinarian in charge.

The preparation of compounds of formula (I) is further illustrated in the following examples.

Hereinafter, TLC is thin layer chromatography, THF is tetrahydrofuran, TFA is trifluoroacetic acid and m.p. is melting point. Where melting points are given, these are uncorrected. The structures of the compounds are confirmed by assignment of 400 MHz NMR spectra (from which representative peaks are quoted) and by microanalysis where appropriate. Compounds used as starting materials are either known compounds or compounds which can be prepared by methods known per se. Column chromatography was carried out using the technique described by Still, W. C. et al., Journal of Organic Chemistry, 1978, 43, 2923 on Merck silica gel 60 (Art 9385). HPLC was carried out on a Waters model 510 chromatograph interfaced via a system module to a Waters 490 multiwavelength detector to a reversed phase $C_{18}$ column (250×4 mm, 5 μm, 100 Å; eluent flow rate 1 ml/min). Retention times are given in minutes.

EXAMPLE 1

2-Chloro-N-[(R)-1-(2-thiazolyl)thio-2-propyl] adenosine

The title compound was prepared according to general method A.

2',3',5'-Tri-O-benzoyl-2-chloro-N-[(R)-1-(thiazolyl) thio-2-propyl]adenosine

To a suspension of 2-[(R)-N-tert-butyloxycarbonyl] amino-1-propanol (4.0 g, 23 mmol), 2-mercaptothiazole (2.9 g, 25 mmol) and triphenylphosphine (7.3 g, 28 mmol) in dry toluene (50 ml) under nitrogen, a solution of diisopropylazocarboxylate (4.9 g, 28 mmol) in dry toluene (30 ml) was added dropwise. The reaction mixture was stirred for 40 h at 20° C. and filtered. The filtrate was evaporated to an oil prior to purification by "flash" chromatography. Elution with a mixture of heptane and ethyl acetate (3:2) provided 2-[2-(R)-tert-butyloxycarbonylamino-1-propylthio]thiazole (3.0 g, 48%) as an oil, TLC $R_f$ 0.33 [heptane/ethyl acetate (3:2)].

2-[2-(R)-tert-butyloxycarbonylamino-1-propylthio] thiazole (3.0 g, 11 mmol) was dissolved in ethyl acetate (30 ml) and a 6N solution of hydrochloric acid in dry ethyl acetate (15 ml) was added. After 20 h at room temperature the reaction mixture was filtered to provide crude 2-[(R)-2-aminopropyl-1-propylthio]thiazole as a hygroscopic, apparent dihydrochloride salt (2.3 g).

To a solution of 9-(2,3,5-tri-O-benzoyl-β-D-ribofuranosyl)-2,6-dichloro-9H-purine (1.5 g, 2.4 mmol) in dry dioxan (50 ml), the above 2-[(R)-2-aminopropyl-1-propylthio]thiazole dihydrochloride (1.5 g, 7.1 mmol) and triethylamine (0.78 g, 7.7 mmol) were introduced at 20° C. After stirring at 50° C. for 40 h the reaction mixture was concentrated to a yellow oil, which was purified by flash chromatography eluting with a mixture of heptane and ethyl acetate (1:1), to afford the title 2',3',5'-tri-O-benzoyl-2-chloro-N-[(R)-1-(2-thiazolyl)thio-2-propyl]adenosine (1.2 g, 63%) as a foam, TLC $R_f$ 0.19 [SiO$_2$; heptane/ethyl acetate (1:1)].

2-Chloro-N-[(R)-1-(2-thiazol)thio-2-propyl)] adenosine

2',3',5'-Tri-O-benzoyl-2-chloro-N-[(R)-1-(2-thiazolyl) thio-2-propyl]adenosine (1.2 g, 1.5 mmol) was dissolved in methanolic ammonia (25 ml) (previously saturated at −10° C.) and stirred at 20° C. for 40 h. The reaction mixture was concentrated to an oil at reduced pressure and purified by flash chromatography eluting with a mixture of dichloromethane, ethanol and ammonia (90:10:1), to provide the title 2-chloro-N-[(R)-1-(2-thiazolyl)thio-2-propyl)] adenosine (0.32 g, 46%) as a foam, $^1$H NMR (DMSO-d$_6$) δ1.31 (3H, d, CHC$\underline{H}_3$), 3.95 (1H, q, H-4'), 4.12 (1H, q, H-3'), 4.51 (1H, q, H-2'), 5.07 (1H, t, 5'-OH), 5.22, 5.50 (2H, 2d, 2'-and 3'-OH), 5.82 (1H, d, H-1'), 7.63 (1H, d, Ar—H), 7.72 (1H, d, Ar—H), 8.41 (1H, s, H-8), 8.48 (1H, d, N—H).

$C_{16}H_{19}ClN_6O_4S_2 \cdot H_2O$ requires C, 41.1; H, 4.3; N, 18.0. Found: C, 41.2; H, 4.3; N, 17.4%.

EXAMPLE 2

2-Chloro-N-[(R)-1-(1-methyl-2-imidazolyl)thio-2-propyl]adenosine

The title compound was prepared according to method A as described above in Example 1 by reacting (R)-1-(1-methyl-2-imidazolyl)thio-2-propylamine hydrochloride [prepared using the same method as described in Example 1 from 2-mercapto-1-methylimidazole (3.31 g, 29 mmol) and 2-[(R)-N-tert-butyloxycarbonyl]amino-1-propanol (5.08 g, 29 mmol) followed by acidic hydrolysis] (2.30 g, 11.1 mmol) with 9-(2,3,5-tri-O-acetyl-β-D-ribofuranosyl)-2,6-dichloro-9H-purine (2.46 g, 5.5 mmol), followed by debenzoylation of the purified product using methanolic ammonia.

This provided the title 2-chloro-N-[(R)-1-(1-methyl-2-imidazolyl)thio-2-propyl]adenosine (1.1 g, 43%) as a foam after column chromatography. $^1$H NMR (DMSO-d$_6$) δ1.28 (3H, d, —CHC$\underline{H}_3$), 3.53–3.60 (1H, m, H-5'$_a$), 3.63–3.70 (1H, m, H-5'$_b$), 3.95 (1H, q, H-4'), 4.13 (1H, q, H-3'), 4.51 (1H, q, H-2'), 5.07 (1H, t, 5'-OH), 5.22, 5.50 (2H, 2d, 2'-and 3'-OH, 5.82 (1H, d, H-1'), 6.92 (1H, s, Ar—H) 7.20 (1H, s, Ar—H), 8.40 (1H, s, H-8), 8.55 (1H, s, N—H). HPLC retention time 19.3 min [gradient elution, 20–80% acetonitrile/water (containing 0.1% TFA)].

C$_{17}$H$_{22}$ClN$_7$O$_4$S. 1.0 H$_2$O requires C, 43.1; H, 5.1; N, 20.7. Found: C, 43.4; H, 5.0; N, 20.7%.

EXAMPLE 3

2-Chloro-N-{(R)-1-[5-methyl-(1,3,4-thiadiazol-2-yl)]thio-2-propyl}adenosine

The title compound was prepared according to method A as described above in Example 1 by reacting 2-[(R)-2-amino-1-propylthio]-5-methyl-[1,3,4]-thiadiazole hydrochloride [prepared by alkylation of 2-mercapto-5-methyl-(1,3,4)-thiadiazole (1.32 g, 10 mmol) using methanesulphonic acid, 2-[(R)-N-tert-butyloxycarbonylamino]-1-propyl ester (3.04 g, 12 mmol) followed by acidic hydrolysis] (1.01 g, 4.47 mmol) with 9-(2,3,5-tri-O-benzoyl-β-D-ribofuranosyl)-2,6-dichloro-9H-purine (2.36 g, 3.73 mmol), followed by debenzoylation of the purified product using methanolic ammonia. This provided the title 2-chloro-N{(R)-1-[5-methyl-(1,3,4-thiadiazol-2-yl)]thio-2-propyl}adenosine (0.94 g, 53%) as a foam after column chromatography. $^1$H NMR (DMSO-d$_6$)δ1.35 (3H, d, —CHC$\underline{H}_3$), 2.67 (3H, s, —CH$_3$), 3.53–3.61 (2H, m, H-5'$_a$ and H-5'$_b$), 3.96 (1H, q, H-4), 4.14 (1H, q, H-3'), 4.52 (1H, q, H-2'), 5.07 (1H, t, 5'-OH), 5.22, 5.50 (2H, 2d, 2'- and 3'-OH), 5.83 (1H, d, H-1'), 8.33–8.46 (2H, m, H-8 and —NH). HPLC retention time 9.9 min [gradient elution, 20–80% acetonitrile/water (containing 0.1% TFA)].

EXAMPLE 4

N-[(R)-1-(2-Benzoxazolyl)thio-2-propyl]-2-chloroadenosine

The title compound was prepared essentially according to method A as described above in Example 1 by reacting 2-[(R)-2-amino-1-propylthio]benzoxazole hydrochloride [prepared by alkylation of 2-mercaptobenzoxazole (3.5 g, 23 mmol) using methanesulphonic acid, 2-[(R)-N-tert-butyloxycarbonylamino]-1-propyl ester (7.2 g, 30 mmol) followed by acidic hydrolysis] (1.7 g, 6 mmol) with 9-(2,3,5-tri-O-acetyl-β-D-ribofuranosyl)-2,6-dichloro-9H-purine (2.7 g, 6.0 mmol), followed by deacylation of the purified product using sodium methoxide in methanol. This provided the title N-[(R)-1-(2-benzoxazolyl)thio2-propyl]-2-chloroadenosine (0.37 g, 28%) as a foam after column chromatography. $^1$H NMR (DMSO-d$_6$) δ1.38 (3H, d, —CHC$\underline{H}_3$), 3.40–3.75 (4H, m, H-5'$_a$ and H-5'$_b$ and —CH$_2$—), 3.94 (1H, q, H-4), 4.12 (1H, q, H-3'), 4.52 (1H, m, H-2'), 5.06 (1H, t, 5'-OH), 5.22, 5.49 (2H, 2d, 2'- and 3'-OH), 5.82 (1H, d, H-1'), 7.26–7.35 (2H, m, Ar—H), 7.53–7.64 (2H, m, Ar—H), 8.39 (1H, s, H-8), 8.48 (1H, d, —NH).

C$_{20}$H$_{21}$ClN$_6$O$_5$S. 0.25 EtOh requires C, 48.8; H, 4.5; N, 16.6. Found: C, 48.6; H, 4.5; N, 16.5%.

EXAMPLE 5

N-[(R)-1-(2-Benzothiazolyl)thio-2-propyl]2-chloroadenosine

The title compound was prepared according to general method A as described above in Example 1 by reacting 2-[(R)-2-amino-1-propylthio]benzothiazole hydrochloride [prepared by a Mitsunobu reaction as described in Example 1 using 2-[(R)-N-tert-butyloxycarbonyl]amino-1-propanol (2.5 g, 14 mmol) and 2-mercaptobenzothiazole (2.3 g, 14 mmol) followed by acidic hydrolysis] (1.7 g, 5.7 mmol) with 9-(2,3,5-tri-O-benzoyl-β-D-ribofuranosyl)-2,6-dichloro-9H-purine (2.8 g, 4.5 mmol), followed by debenzoylation of the purified 2',3',5'-tri-O-benzoyl-2-chloro-N-[(R)-1-(2-benzothiazolyl)thio-2-propyl]adenosine in methanolic ammonia (200 ml) (previously saturated at −10° C.) to provide the title 2-chloro-N-[(R)-1-(2-benzothiazolyl)thio-2-propyl]adenosine (1.05 g, 24%) (following column chromatography), $^1$H NMR (DMSO-d$_6$) δ1.38 (3H, d, —CHC$\underline{H}_3$), 3.50–3.68 (4H, m, H-5'$_a$ and H-5'$_b$ and —CH$_2$—), 3.95 (1H, d, H-4'), 4.12 (1H, d, H-3'), 4.51 (1H, q, H-2'), 5.07 (1H, t, 5'-OH), 5.22, 5.50 (2H, 2d, 2'- and 3'-OH), 5.83 (1H, d, H-1'), 7.34, 7.45 (2H, 2t, Ar—H), 7.85, 7.98 (2H, 2d, Ar—H), 8.40 (1H, s, H-8), 8.53 (1H, d, N—H). HPLC retention time 16.6 min [gradient elution, 20–80% acetonitrile/water (containing 0.1% TFA)].

C$_{20}$H$_{21}$ClN$_6$O$_4$S$_2$.0.5 EtOH requires C, 47.4; H, 4.5; N, 15.8. Found: C, 47.3; H, 4.5; N, 15.8%.

EXAMPLE 6

N-[(S)-1-(2-Benzothiazolyl)thio-2-propyl]-2-chloroadenosine

The title compound was prepared according to general method A as described above in Example 1 by reacting 2-[(S)-2-amino-1-propylthio]benzothiazole hydrochloride [prepared by a Mitsunobu reaction as laid out in Example 1 using 2-[(S)-N-tert-butyloxycarbonyl]amino-1-propanol (3.5 g, 20 mmol) and 2-mercaptobenzothiazole (3.35 g, 20 mmol) followed by acidic hydrolysis] (1.1 g, 4.2 mmol) with 9-(2,3,5-tri-O-benzoyl-β-D-ribofuranosyl)-2,6-dichloro-9H-purine (2.8 g, 4.5 mmol), followed by debenzoylation of the purified 2',3',5'-tri-O-benzoyl-2-chloro-N-[(S)-1-(2benzothiazolyl)thio-2-propyl]adenosine using sodium methoxide in methanol to provide the title 2-chloro-N-[(S)-1-(2-benzothiazolyl)thio-2-propyl]adenosine (0.88 g, 49%) (following column chromatography), $^1$H NMR (DMSO-d$_6$) δ1.38 (3H, d, —CHC$\underline{H}_3$), 3.50–3.68 (4H, m, H-5'$_a$ and H-5'$_b$ and —CH$_2$—), 3.95 (1H, d, H-4'), 4.12 (1H, d, H-3'), 4.51 (1H, q, H-2'), 5.07 (1H, t, 5'-OH), 5.22, 5.50 (2H, 2d, 2'-and 3'-OH), 5.83 (1H, d, H-1'), 7.34, 7.45 (2H, 2t, Ar—H), 7.85, 7.98 (2H, 2d, Ar—H), 8.40 (1H, s, H-8), 8.52 (1H, s, N—H). HPLC retention time 20.1 min [gradient elution, 20–80% acetonitrile/water (containing 0.1% TFA)].

C$_{20}$H$_{21}$ClN$_6$O$_4$S$_2$.1.5 H$_2$O requires C, 44.8; H, 4.5; N, 15.7. Found: C, 44.9; H, 4.1; N, 15.2%.

EXAMPLE 7

N-[(R)-1-(2-Benzothiazolyl)thio-2-propyl]-2-bromoadenosine

The title compound was prepared according to general method A as described above in Example 1 by reacting 2-[(R)-2-amino-1-propylthio]benzothiazole hydrochloride (prepared as indicated in Example 5) (1.07 g, 3.6 mmol) with 2-bromo-9-(2,3,5-tri-O-acetyl-β-D-ribofuranosyl)-6-chloro-9H-purine (see WO 93/08206; Bioorganic and Medicinal Chemistry Letters, 1993, 3, 2661–2666) (1.48 g, 3.0 mmol) followed by deacylation of the purified 2',3',5'-tri-O-acetyl-2-bromo-N-[(R)-1-(2-benzothiazolyl)thio-2-propyl]adenosine using sodium methoxide in methanol to provide the title N-[(R)-1-(2-benzothiazolyl)thio-2-propyl]-

15

2-bromoadenosine (0.20 g, 14%) as a foam (following column chromatography), $^1$H NMR (DMSO-$d_6$) δ1.38 (3H, d, —CHC$\underline{H}_3$), 3.50–3.77 (4H, m, H-5'$_a$ and H-5'$_b$ and —CH$_2$—), 3.94 (1H, d, H-4'), 4.12 (1H, d, H-3'), 4.51 (1H, q, H-2'), 4.70 1H, m, —C$\underline{H}$CH$_3$), 5.05 (1H, t, 5'-OH), 5.22, 5.49 (2H, 2d, 2'- and 3'-OH), 5.83 (1H, d, H-1'), 7.36, 7.46 (2H, 2t, Ar—H), 7.86, 7.99 (2H, 2d, Ar—H), 8.40 (1H, s, H-8). HPLC retention time 6.74 min [gradient elution, 20–80% acetonitrile/water (containing 0.1% TFA)].

$C_{20}H_{21}N_6BrO_4S_2$.0.1 $H_2O$ requires C, 43.3; H, 3.8; N, 15.1. Found: C, 43.7; H, 4.3; N, 14.7%.

EXAMPLE 8

N-[(R)-1-(2-Benzothiazolyl)thio-2-propyl]-2-methyladenosine

The title compound was prepared according to general method A as described above in Example 1 by reacting 2-[(R)-2-amino-1-propylthio]benzothiazole hydrochloride (prepared as described in Example 5) (0.89 g, 3.0 mmol) with 9-(2,3,5-tri-O-acetyl-β-D-ribofuranosyl)-6-chloro-2-methyl-9H-purine (1.07 g, 2.5 mmol) [prepared from 2-methylinosine (Journal of Organic Chemistry, 1967, 32, 3258–3260) by standard acylation and chlorination steps]. Deacylation of the purified 2',3',5'-tri-O-acetyl-N-[(R)-1-(2-benzothiazolyl)thio-2-propyl]-2-methyladenosine using sodium methoxide in methanol to provide the desired N-[(R)-1-(2-benzothiazolyl)thio-2-propyl]-2-methyladenosine (0.28 g, 11%) (following column chromatography), $^1$H NMR (DMSO-$d_6$) δ1.40 (3H, d, —CHC$\underline{H}_3$), 2.30 (3H, s, —CH$_3$), 3.50–3.77 (4H, m, H-5'$_a$ and H-5'$_b$ and —CH$_2$—), 3.98 (1H, d, H-4'), 4.13 (1H, d, H-3'), 4.63 (1H, q, H-2'), 4.86 (1H, br, —CHC$\underline{H}_3$), 5.19, 5.42 (2H, 2d, 2'- and 3'-OH), 5.70 (1H, t, 5'-OH), 5.85 (1H, d, H-1'), 7.36, 7.47 (2H, 2t, Ar—H), 7.80–7.96 (2H, m, Ar—H), 8.0 (1H, s, N—H), 8.26 (1H, s, H-8), 8.52 (1H, s, N—H). HPLC retention time 22.4 min [gradient elution, 20–80% acetonitrile/water (containing 0.1% TFA)].

$C_{21}H_{24}N_6O_4S_2$.$H_2O$ requires C, 49.8; H, 4.8; N, 16.6. Found: C, 49.9; H, 5.1; N, 16.4%.

EXAMPLE 9

N-[(R)-1-(2-benzothiazolyl)thio-2-propyl]-2-methylthioadenosine

The title compound was prepared according to general method A. 9-(2,3,5-Tri-O-acetyl-β-D-ribofuranosyl)-2-amino-6-chloro-9H-purine (Nucleic Acid Chemistry, Townsend L. B. and Tipson, R. S., eds., John Wiley and Sons Inc., 1986, 3, 144) (4.0 g, 9.3 mmol) was dissolved in acetonitrile (100 ml). Isoamylnitrite (10.84 g, 93 mmol) was introduced followed by methyl disulphide (4.14 ml, 46 mmol) and the reaction mixture was heated at an oil bath temperature of 100° C. for 2 h. The evolved gas was oxidised using a hypochlorite scrubber. The reaction mixture was cooled, evaporated and purified by flash chromatography on silica gel. Elution initially with dichloromethane, followed by dichloromethane/methanol (100:1) provided 9-(2,3,5-tri-O-acetyl-β-D-ribofuranosyl)-6-chloro-2-methylthio-9H-purine (3.1 g, 72%) as a foam, $^1$H NMR (CDCl$_3$) δ2.12, 2.14, 2.18 (9H, 3s, 2',3' and 5'-O-acetyl CH$_3$), 2.66 (3H, s, —SCH$_3$), 4.28–4.51 (3H, m, H-5'$_a$, H-5'$_b$ and H-4'), 5.66 (1H, t, H-3'), 6.0 (1H, t, H-2'), 6.13 (1H, d, H-1'), 8.11 (1H, s, H-8).

The above 9-(2,3,5-tri-O-acetyl-β-D-ribofuranosyl)-6-chloro-2-methylthio-9H-purine (0.5 g, 1.1 mmol) was reacted with 2-[(R)-2-amino-1-propylthio]benzothiazole hydrochloride (0.5 g, 1.5 mmol) (by the procedure described in Example 5) followed by deacylation of the purified 2',3',5'-tri-O-acetyl-N-[(R)-1-(2-benzothiazolyl)thio-2-propyl]-2-methylthioadenosine using methanolic ammonia (200 ml) (previously saturated at −10° C.) to provide the title compound N-[(R)-1-(2-benzothiazolyl)thio-2-propyl]-2methylthioadenosine (0.085 g, 16%) as a foam (following column chromatography), $^1$H NMR (DMSO-$d_6$) δ1.39 (3H, d, —CHC$\underline{H}_3$), 2.31 (3H, s, —SCH$_3$), 3.46–3.71 (4H, m, H-5'$_a$ and H-5'$_b$ and —CH$_2$), 3.92 (1H, q, H-4'), 4.14 (1H, q, H-3'), 4.60 (1H, q, H-2'), 4.70–4.91 (1H, m, —CH), 5.05 (1H, t, 5'-OH), 5.22, 5.45 (2H, 2d, 2'- and 3'-OH), 5.83 (1H, d, H-1'), 7.31–7.53 (2H, m, Ar—H), 7.84, 8.0 (2H, 2d, Ar—H), 8.10 (1H, d, N—H), 8.25 (1H, s, H-8).

EXAMPLE 10

N$^6$-[(R)-1-(2-Benzothiazolyl)thio-2-propyl]-2-(dimethylamino)adenosine

The title compound was prepared according to general method B by reaction of N-[(R)-1-(2-benzothiazolyl)thio-2-propyl]-2-chloroadenosine (1.02 g, 2.0 mmol) (Example 5) in dimethylformamide (10 ml) to provide the desired N-[(R)-1-(2-benzothiazolyl)thio-2-propyl]-2-(dimethylamino)adenosine (0.12 g, 12%) as a foam (following column chromatography), $^1$H NMR (DMSO$_6$) δ1.38 (3H, d, —CHC$\underline{H}_3$), 2.92 (6H, s, —N(CH$_3$)$_2$), 3.40–3.72 (4H, m, H-5'$_a$ and H-5'$_b$ and —CH$_2$—), 3.88 (1H, q, H-4'), 4.15 (1H, q, H-3'), 4.65 (1H, q, H-2'), 4.72–4.85 (1H, m, —CH—), 4.89 (1H, t, 5'-OH), 5.14, 5.36 (2H, 2d, 2'- and 3'-OH), 5.75 (1H, d, H-1'), 7.35, 7.46 (2H, 2 t, Ar—H), 7.50 (1H, d, N—H), 7.84, 7.99 (2H, 2d, Ar—H), 7.94 (1H, s, H-8). HPLC retention time 16.8 min [gradient elution, 20–80% acetonitrile/water (containing 0.1% TFA)].

$C_{22}H_{26}N_7O_4S_2$.0.5 $H_2O$ requires C, 50.2; H, 5.2; N, 18.6. Found: C, 50.5; H, 5.7; N, 18.2%.

EXAMPLE 11

N$^6$-[(R)-1-(2-Benzothiazolyl)thio-2-propyl]-2-(ethylamino)adenosine

The title compound was prepared according to general method B by reaction of N-[(R)-1-(2-benzothiazolyl)thio-2-propyl]-2-bromoadenosine (Example 7) (0.24 g, 0.35 mmol) with 70% w/w aqueous ethylamine (0.23 g) in dioxan (10 ml) in a sealed vessel at 100° C. to provide the desired N-[(R)-1-(2-benzothiazolyl)thio-2-propyl]-2-(ethylamino) adenosine as a foam (following column chromatography), $^1$H NMR (DMSO-$d_6$) δ1.04 (3H, br t, —NCH$_2$C$\underline{H}_3$), 1.42 (3H, d, —CHC$\underline{H}_3$), 3.20 (3H, br m, —NC$\underline{H}_2$CH$_3$), 3.55–3.80 (4H, m, H-5'$_a$ and H-5'$_b$ and —CH$_2$—), 3.95 (1H, q, H-4'), 4.15 (1H, q, H-3'), 5.16, 5.41 (2H, 2d, 2'- and 3'-OH), 5.79 (1H, d, H-1'), 6.22 (1H, t, —N$\underline{H}$CH$_2$CH$_3$), 7.43, 7.54 (2H, 2 t, Ar—H), 7.98 (1H, s, H-8). HPLC retention time 17.0 min [gradient elution, 20–80% acetonitrile/water (containing 0.1% TFA)].

EXAMPLE 12

2-Amino-N$^6$-[(R)-1-(2-benzothiazolyl)thio-2-propyl] adenosine

The title compound was prepared according to general method A as described above in Example 1 by reacting 2-[(R)-2-amino-1-propylthio]benzothiazole hydrochloride (prepared as described in Example 5) (7.13 g, 24 mmol) with 2-amino-9-(2,3,5-tri-O-acetyl-β-D-ribofuranosyl)-6-chloro-9H-purine (Nucleic Acid Chemistry, Townsend L. B. and Tipson, R. S., eds., John Wiley and Sons Inc., 1986, 3, 144) (8.56 g, 20 mmol) followed by deacylation of a portion of the purified 2',3',5'-tri-O-acetyl-2-amino-N-[(R)-1-(2-benzothiazolyl)thio-2-propyl]adenosine using sodium methoxide in methanol to provide the title 2-amino-N-[(R)-1-(2-benzothiazolyl)thio2-propyl]adenosine (0.71 g, 19%) as a foam (following column chromatography) $^1$H NMR (DMSO-$d_6$) δ1.34 (3H, d, —CHC$H_3$), 3.50–3.73 (4H, m, H-5'$_a$- and H-5'$_b$ and —CH$_2$—), 3.90 (1H, q, H-4'), 4.10 (1H, d, H-3'), 4.51 (1H, q, H-2'), 5.11, 5.37 (2H, 2d, 2'- and 3'-OH), 5.40 (1H, t, 5'-OH), 5.73 (1H, d, H-1'), 5.79 (1H, br, —NH$_2$), 7.36, 7.47 (2H, 2t, Ar—H), 7.92 (1H, s, H-8), 8.0 (1H, d, N—H). HPLC retention time 13.5 min [gradient elution, 20–80% acetonitrile/water (containing 0.1% TFA)].

EXAMPLE 13

N-[(R)-1-(2-Benzothiazolyl)thio-2-propyl]-2-fluoroadenosine

The title compound was prepared according to general method C by reacting 9-(2,3,5-tri-O-acetyl-β-D-ribofuranosyl)-2-amino-6-chloro-9H-purine (see Example 9) (0.45 g, 0.73 mmol) using the diazotisation/fluoroboric acid method described previously (see WO 93/08206; Bioorganic and Medicinal Chemistry Letters, 1993, 3, 2661–2666) to provide 2',3',5'-tri-O-acetyl-N-[(R)-1-(2-benzothiazolyl)thio-2-propyl]-2-fluoroadenosine (0.19 g, 43%), followed by deacylation using sodium methoxide in methanol to provide the title N-[(R)-1-(2-benzothiazolyl)thio-2-propyl]-2-fluoroadenosine (0.088 g) (following column chromatography), $^1$H NMR (DMSO-$d_6$) δ1.37 (3H, d, —CHC$H_3$, 3.50–3.79 (4H, m, H-5'$_a$ and H-5'$_b$ and —CH$_2$—), 3.95 (1H, d, H-4'), 4.13 (1H, m, H-3'), 4.51 (1H, q, H-2'), 4.67 (1H, br, —C$H$CH$_3$), 5.07 (1H, t, 5'-OH), 5.23, 5.50 (2H, 2d, 2'- and 3'-OH), 5.79 (1H, d, H-1'), 7.37, 7.48 (2H, 2t, Ar—H), 7.85, 7.79 (2H, 2d, Ar—H), 8.36 (1H, s, H-8), 8.58 (1H, d, N—H). HPLC retention time 18.9 min [gradient elution, 20–80% acetonitrile/water (containing 0.1% TFA)].

$C_{20}H_{21}FN_6O_4S_2$. 1.25 $H_2O$ requires C, 46.6; H, 4.1; N, 16.3. Found: C, 46.5; H, 4.5; N, 16.3%.

EXAMPLE 14

N-[(S)-2-(2-Benzothiazolyl)thio-1-propyl]-2-chloroadenosine (S)-(2-Benzothiazolyl)thio-1-propylamine (1.5 g, 5.0 mmol) (prepared by the method described in Example 1 from (S)-2-hydroxypropylamine) was reacted with 9-(2,3,5-tri-O-acetyl-β-D-ribofuranosyl)-2,6-dichloro-9H-purine (1.49 g, 2.4 mmol) in dioxan (20 ml) in the presence of triethylamine (2.77 ml, 20 mmol) to provide 2',3',5'-tri-O-acetyl-N-[(S)-2-(2-benzothiazolyl)thio-1-propyl]-2-chloroadenosine, which was deacylated using methanolic ammonia (previously saturated at –10° C.) to provide the title N-[(S)-2-(2-benzothiazolyl)thio-1-propyl]-2-chloroadenosine (0.78 g, 47%) as a foam (following column chromatography), $^1$H NMR (DMSO-$d_6$) δ1.52 (3H, d, —CH$_3$), 3.56 (1H, ABX, H-5'$_a$), 3.68 (1H, m, H-5'$_b$), 3.73–3.91 (1H, m, —C—H), 3.84–3.92 (1H, m, —C—H), 3.96 (1H, q, H-4'), 4.15 (1H, m, H-3'), 4.53 (1H, dd, H-2'), 5.08 (1H. t, 5'-OH), 5.23, 5.50 (3H, 3 br, 2' and 3'-OH), 5.84 (1H, d, H-1'), 7.36, 7.47 (2H, 2, Ar—H), 7.83, 7.99 (2H, 2d, Ar—H), 8.40 (1H, s, H-8), 8.72 (1H, t, N—H), HPLC retention time 17.8 min [gradient elution, 20–80% acetonitrile/water (containing 0.1% TFA)].

$C_{20}H_{21}ClN_6O_4S_2$. 0.5$H_2O$ 0.1 EtOAc requires C, 46.5; H, 4.4; N, 16.0. Found: C, 46.6; H, 4.4; N, 15.8%.

EXAMPLE 15

N-[(R)-1-(2-Benzothiazolyl)thio-2-butyl]-2-chloroadenosine

The title compound was prepared according to general method A as described above in Example 1 by reacting 2-[(R)-2-amino-1-butylthio]benzothiazole hydrochloride (1.16 g, 4.2 mmol) with 9-(2,3,5-tri-O-acetyl-β-D-ribofuranosyl)-2,6-dichloro-9H-purine (1.57 g, 3.5 mmol), followed by deacylation of the purified 2',3',5'-tri-O-acetyl-2-chloro-N-[(R)-1-(2-benzothiazolyl)thio-2-propyl]adenosine using sodium methoxide in methanol. This provided the title N-[(R)-1-(2-benzothiazolyl)thio-2-butyl]-2-chloroadenosine (0.93 g, 51%) (following column chromatography), $^1$H NMR (DMSO-$d_6$) δ1.38 (3H, d, —CH$_2$C$H_3$), 1.65–1.86 (2H, m, —C$H_2$CH$_3$), 3.95 (1H, q, H-4'), 4.14 (1H, d, H-3'), 4.48–4.62 (2H, m, H-2' and —C$H$CH$_2$H$_3$), 5.07 (1H, t, 5'-OH), 5.22, 5.50 (2H, 2d, 2'- and 3'-OH), 5.83 (1H, d, H-1'), 7.34, 7.45 (2H, 2t, Ar—H), 7.84, 8.0 (2H, 2d, Ar—H). HPLC retention time 21.8 min [gradient elution, 20–80% acetonitrile/water (containing 0.1% TFA)].

$C_{21}H_{23}ClN_6O_4S_2$. requires C, 48.2; H, 4.4; N, 16.1. Found: C, 47.9; H, 4.5; N, 15.7%.

EXAMPLE 16

N-[1-(2-Benzothiazolyl)thio-3-methyl-2-butyl]-2-chloroadenosine

The title compound was prepared according to general method A as described above in Example 1 by reacting 2-[2-amino-3-methyl-1-butylthio]benzothiazole hydrochloride (1.37 g, 4.2 mmol) with 9-(2,3,5-tri-O-acetyl-β-D-ribofuranosyl)-2,6-dichloro-9H-purine (1.57 g, 3.5 mmol), followed by deacylation of the purified 2',3',5'-tri-O-acetyl-2-chloro-N-[1-(2-benzothiazolyl)thio-2-propyl]adenosine using sodium methoxide in methanol. This provided the title N-[1-(2-benzothiazolyl)thio-3-methyl-2-butyl]-2-chloroadenosine (0.69 g, 37%) as a foam (mixture of diastereoisomers) (following column chromatography), $^1$H NMR (DMSO-$d_6$) δ0.97–1.05 [6H, m, —CH(C$H_3$)$_2$], 2.0–2.13 [1H, m, —C$H$(CH$_3$)$_2$], 3.50–3.70 (3H, m, H-5'$_a$ and H-5'$_b$ and —CH—), 3.88–3.97 (2H, m, H-4' and —CH—), 5.02, 5.06 (1H, 2t, 5'-OH), 5.21, 5.50 (2H, 2d, 2'- and 3'-OH), 5.32 (1H, dd, H-1'), 7.36, 7.46 (2H, 2t, Ar—H). HPLC retention time 23.8 min [gradient elution, 20–80% acetonitrile/water (containing 0.1% TFA)].

$C_{22}H_{25}ClN_6O_4S_2$. requires C, 49.2; H, 4.7; N, 15.7. Found: C, 49.3; H, 5.0; N, 15.4%.

EXAMPLE 17

N-[3-(2-Benzothiazolyl)thio-1,1,1-trifluoro-2-propyl]-2-chloroadenosine

The title compound was prepared according to method A. 2-(N-tert-butyloxycarbonyl)amino-1,1,1-trifluoro-3-propanol was prepared by reaction of 2-hydroxymethyl-3,3,3-trifluoropropionic acid (3.16 g, 20 mmol) with diphenylphosphoryl azide (5.50 g, 20 mmol) in tert-butanol. The resultant 4-(trifluoromethyl)oxazolidin-2-one was treated with hydrochloric acid to afford 2-amino-3,3,3-trifluoropropanol. This amine was N-Boc protected under standard conditions (see Example 18) to provide 2-(N-tertbutyloxycarbonyl)amino-1,1,1-trifluoro-3-propanol (0.65 g), TLC R$_f$ 0.37 [SiO$_2$; ethyl acetate/cyclohexane (1:1)].

N-[3-(2-Benzothiazolyl)thio-1,1,1-trifluoro-2-propyl]-2-chloroadenosine was prepared according to general method A as described in Example 1 by reacting 2-[(R)-2-amino-1,1,1 trifluoro-3-propylthio]benzothiazole hydrochloride [prepared by a Mitsunobu reaction as described in Example 1 using the above 2-(N-tert-butyloxycarbonyl)amino-1,1,1-trifluoro-3-propanol and 2-mercaptobenzothiazole followed by acidic hydrolysis] (0.13 g, 0.47 mmol) with 9-(2,3,5-tri-O-acetyl-β-D-ribofuranosyl)-2,6-dichloro-9H-purine (0.21 g, 0.45 mmol). Debenzoylation of the purified 2',3',5'-tri-O-acetyl-N-[3-(2-benzothiazolyl)thio-1,1,1-trifluoro-2-propyl] -2-chloroadenosine in methanolic ammonia (20 ml) (previously saturated at −10° C.) provided the title N-[3-(2-benzothiazolyl)thio-1,1,1-trifluoro-2-propyl]-2-chloroadenosine (0.12 g, 45%) (following column chromatography) [a mixture of (R)- & (S)-diastereoisomers]; $^1$H NMR (DMSO-d$_6$) δ3.39–3.49 (1H, m, —CH), 3.58, 3.68 (2H, ABX, H-5'$_a$ and H-5'$_b$), 3.98 (1H, q, H-4'), 4.11–4.18 (2H, m, H-3' and —CH—), 4.47–4.56 (1H, m, H-2'), 5.08 (1H, m, 5'-OH), 5.18–5.28 (1H, m, —CHCH$_2$—), 5.27, 5.57 (2H, 2d, 2'- and 3'-OH), 5.94 (1H, d, H-1'), 7.08, 7.22, 7.30 (3H, 3 t, Ar—H), 7.71 (1H, d, Ar—H), 8.75 (1H, s, H-8), 8.79 (1H, d, N—H).

EXAMPLE 18 trans-N-[2-[(2-Benzothiazolyl)thio]cyclopentyl]-2-chloroadenosine trans-N-(tert-Butyloxycarbonyl)-2-hydroxycyclopentylamine (see WO 93/23418) was prepared as a mixture of enantiomers by reaction of cyclopentene epoxide (8.0 g, 95.1 mmol) with a 25% aqueous ammonia solution (35 ml) in a sealed glass vessel at 110° C. for 1.5 h. The reaction mixture was cooled and evaporated to half its original volume before 1N sodium hydroxide solution (95 ml) and THF (100 ml) were introduced at 0° C. A solution of di-tert-butyl dicarbonate (21.8 g, 99.6 mmol) in THF (50 ml) was added dropwise and the reaction mixture stirred at room temperature for 18 h. The phases were separated and the aqueous phase was washed with ethyl acetate (100 ml). The organic phases were combined and washed with saturated brine (100 ml), dried (MgSO$_4$) and evaporated. The solid residue was recrystallised from a 10:1 mixture of heptane and ethyl acetate (55 ml) to provide an analytical sample of trans-N-(tert-butyloxycarbonyl)-2-hydroxycyclopentylamine (4.06 g, 21%), mp 103°–105° C.

C$_{10}$H$_{19}$NO$_3$ requires C, 59.7; H, 9.5; N, 7.0. Found: C, 59.6; H, 9.8; N, 7.0%.

The above trans-N-(tert-butyloxycarbonyl)-2-hydroxycyclopentylamine (24.7 g, 123 mmol) (prepared as described in Example 11) was dissolved in THF (500 ml) and 4-nitrobenzoic acid (20.51 g, 123 mmol) was added, followed by triphenylphosphine (48.28 g, 184 mmol). A solution of diethylazodicarboxylate (32.06 g, 184 mmol) in THF (250 ml) was introduced dropwise. The reaction mixture was stirred for 18 h at room temperature, evaporated and purified by flash chromatography eluting with a mixture of cycohexane and ethyl acetate (4:1) to provide the intermediate 4-nitrobenzoyl ester as a solid (25.5 g), TLC R$_f$ 0.52 [SiO$_2$:cyclohexane/ethyl acetate (1:1)]. This ester was suspended in a mixture of a mixture of methanol (180 ml) and 25% aqueous ammonia solution (20 ml) and the mixture was stirred at room temperature for 70 h before evaporation to a residue. Purification by flash chromatography eluting with a mixture of cycohexane and ethyl acetate (4:1) provided fractions containing the title compound which crystallised on evaporation to afford cis-N-(tert-butyloxycarbonyl)-2-hydroxycyclopentylamine as a solid (11.0 g, 44%), mp 64°–65° C.

trans-N-[2-[(2-Benzothiazolyl)thio]cyclopentyl]-2-chloroadenosine

The above cis-N-(tert-butyloxycarbonyl)-2-hydroxycyclopentylamine was converted into trans-2-(2-benzothiazolyl)cyclopentylamine hydrochloride by the sequence of reactions described in Example 1 (i.e. thioether formation by the Mitsunobu procedure resulting in inversion at the 2-position, followed by acidic hydrolysis of the N-Boc-group).

This trans-2-(2-benzothiazolyl)cyclopentylamine hydrochloride (1.0 g, 3.0 mmol) was combined with 9-(2,3,5-tri-O-acetyl-β-D-ribofuranosyl)-2,6-dichloro-9H-purine (1.34 g, 3 mmol) and triethylamine (1.66 ml) and reacted using the procedure described in Example 1. Deacylation of the purified [trans]-2',3',5'-tri-O-acetyl-N-[2-[(2-benzothiazolyl)thio]cyclopentyl]-2-chloroadenosine was carried out using methanolic ammonia (200 ml) (previously saturated at −10° C.) which provided the title product as a ca. 1:1 mixture of diastereoisomers, HPLC retention time 24.1 and 24.82 min [isocratic elution, 35% acetonitrile/65% water (containing 0.1% TFA)]. A single diastereoisomer of trans-N-[2-[(2benzothiazolyl)thio]cyclopentyl]-2-chloroadenosine (0.11 g, 7%) was obtained as a foam (following short path column chromatography), $^1$H NMR (DMSO-d$_6$) δ1.65–2.62 (6H, 5m, —CH$_2$CH$_2$CH$_2$—), 3.51–3.58 and 3.62–3.69 (2H, ABX, H-5'$_a$ and H-5'$_b$), 3.94 (1H, br q, H-4'), 4.13 (1H, br q, H-3'), 4.28 (1H, q, —CH—), 4.49 (1H, q, H-2'), 4.68 (1H, m, —CH—), 4.62 (1H, q, H-2'), 5.07 (1H, t, 5'-OH), 5.22, 5.50 (2H, 2d, 2'- and 3'-OH), 5.82 (1H, d, H-1'), 7.35, 7.45 (2H, 2t, Ar—H), 7.79, 7.98 (2H, 2d, Ar—H), 8.40 (1H, s, H-8), 8.71 (1H, d, N—H). HPLC retention time 24.82 min [gradient elution, 20–80% acetonitrile/water (containing 0.1% TFA)].

C$_{22}$H$_{23}$ClN$_6$O$_4$S$_2$. 0.5 EtOH requires C, 49.5; H, 4.7; N, 15.1. Found: C, 49.1; H, 4.8; N, 14.9%.

EXAMPLE 19 cis-N-[2-[(2-Benzothiazolyl)thio]cyclopentyl]-2-chloroadenosine trans-N-(tert-Butyloxycarbonyl)-2-hydroxycyclopentylamine (see Example 16) was converted into cis-2-(2-benzothiazolyl)cyclopentylamine hydrochloride by the sequence of reactions described in Example 1 (i.e. thioether formation by the Mitsunobu procedure resulting in inversion at the cyclopentane 2-position, followed by acidic hydrolysis of the Boc-group) (see also WO 93/23418).

The above cis-2-(2-benzothiazolyl)cyclopentylamine hydrochloride (1.5 g, 4.6 mmol) was combined with 9-(2,3,5-tri-O-acetyl-β-D-ribofuranosyl)-2,6-dichloro-9H-purine (2.0 g, 4.5 mmol) and triethylamine (2.49 ml) and reacted by the method described in Example 1. Deacylation of the purified cis-2',3',5'-tri-O-acetyl-N-[2-[(2-benzothiazolyl)thio]cyclopentyl]-2-chloroadenosine using sodium methoxide in methanol provided the title cis-N-[2-[(2-benzothiazolyl)thio]cyclopentyl]-2-chloroadenosine (0.89 g, 38%) as a foam (following column chromatography) (a ca. 2:1 mixture of diastereoisomers), $^1$H NMR (DMSO-d$_6$) δ1.62–2.45 (6H, 5m, —CH$_2$CH$_2$CH$_2$—), 3.52–3.60 (1H, m, H-5'$_a$), 3.64–3.70 (1H, m, H-5'$_b$), 3.94 (1H, br q, H-4'), 4.11 (1H, br q, H-3'), 4.62 (1H, q, H-2'), 5.75–5.83 (1H, 2m, H-1'), 7.26–7.94 (4H, 4m, Ar—H).

EXAMPLE 20

N-[(R)-1-(6-Amino-2-benzothiazolyl)thio-2-propyl]-2-chloroadenosine

The title compound was prepared according to general method A as described above in Example 1 by reacting 6-amino-2-[(R)-2-aminopropyl-1-propylthio]benzothiazole hydrochloride [prepared by a Mitsunobu reaction as described in Example 1 using 2-[(R)-N-tert-butyloxycarbonyl]amino-1-propanol (13.1 g, 75 mmol) and 6-amino-2-mercaptobenzothiazole (13.7 g, 75 mmol) followed by acidic hydrolysis]) (2.51 g, 7.2 mmol) with 9-(2,3,5-tri-O-acetyl-β-D-ribofuranosyl)-2,6-dichloro-9H-purine (2.68 g, 6.0 mmol), followed by deacylation of the purified 2',3',5'-tri-O-acetyl-N-[(R)-1-(6-amino-2-benzothiazolyl)thio-2-propyl]-2-chloroadenosine in methanolic ammonia (200 ml) (previously saturated at −10° C.) to provide the title N-[(R)- 1-(6-amino2-benzothiazolyl)thio-2-propyl]-2-chloroadenosine (1.97 g, 63%) as a foam (following column chromatography), $^1$H NMR (DMSO-d$_6$) δ1.36 (3H, d, —CHC$\underline{H}_3$), 3.50–3.71 (4H, m, H-5'$_a$ and H-5'$_b$ and —CH$_2$—), 3.95 (1H, d, H-4'), 4.14 (1H, d, H-3'), 4.53 (1H, q, H-2'), 4.63 (1H, m, —CH), 5.08 (1H, t, 5'-OH), 5.22, 5.50 (2H, 2d, 2'- and 3'-OH), 5.83 (1H, d, H-1'), 6.71, 6.99, 7.53 (3H, 3d, Ar—H), 8.41 (1H, s, H-8), 8.52 (1H, d, N—H). HPLC retention time 10.29 min [gradient elution, 20–80% acetonitrile/water (containing 0.1% TFA)].

EXAMPLE 21

2-Chloro-N-[(R)-1-(6-ethoxy-2-benzothiazolyl)thio-2-propyl]adenosine

The title compound was prepared according to general method A as described above in Example 1 by reacting 2-[(R)-2-amino-1-propylthio]-6-ethoxybenzothiazole hydrochloride [prepared by a Mitsunobu reaction as described in Example 1 using 2-[(R)-N-tert-butyloxycarbonyl]amino-1-propanol (3.5 g, 20 mmol) and 6-ethoxy-2-mercaptobenzothiazole (4.23 g, 20 mmol) followed by acidic hydrolysis] (3.8 g, 11.1 mmol) with 9-(2,3,5-tri-O-acetyl-β-D-ribofuranosyl)-2,6-dichloro-9H-purine (1.1 g, 2.5 mmol), followed by deacylation of the purified 2',3',5'-tri-O-acetyl-2-chloro-N-[(R)-1-(6-ethoxy-2-benzothiazolyl)thio-2-propyl]adenosine using sodium methoxide in methanol to provide the title N[(R)-1-(6-ethoxy-2-benzothiazolyl)thio-2-propyl]-2-chloroadenosine (0.22 g, 17%) as a foam (following column chromatography), $^1$H NMR (DMSO-d$_6$) δ1.32–1.40 (6H, m, —CH$_2$C$\underline{H}_3$ and —CHC$\underline{H}_3$), 3.44–3.81 (4H, m, H-5'$_a$ and H-5'$_b$ and —CH$_2$—), 3.97 (1H, d, H-4'), 4.08 (2H, q, —C$\underline{H}_2$CH$_3$), 4.14 (1H, d, H-3'), 4.53 (1H, q, H-2'), 4.68 (1H, m, —CH), 5.09 (1H, t, 5'-OH), 5.23, 5.51 (2H, 2d, 2'- and 3'-OH), 5.83 (1H, d, H-1'), 7.06, 7.57, 7.74 (3H, 3d, Ar—H), 8.42 (1H, s, H-8), 8.53 (1H, d, N—H). HPLC retention time 22.4 min [gradient elution, 20–80% acetonitrile/water (containing 0.1% TFA)].

C$_{22}$H$_{25}$ClN$_6$O$_5$S$_2$. 0.5 H$_2$O. 0.2 EtOAC requires C, 47.2; H, 4.8; N, 14.5. Found: C, 47.3; H, 4.9; N, 14.3%.

EXAMPLE 22

2-Chloro-N-[(R)-1-(5-chloro-2-benzothiazolyl)thio-2-propyl]adenosine

The title compound was prepared according to general method A as described above in Example 1 by reacting 2-[(R)-2-amino-1-propylthio]-5-chlorobenzothiazole hydrochloride [prepared by a Mitsunobu reaction as described in Example 1] with 2-[(R)-N-tert-butyloxycarbonyl]amino-1-propanol (1.75 g, 10 mmol) and 5-chloro-2-mercaptobenzothiazole (2.02 g, 10 mmol) followed by acidic hydrolysis] (0.5 g, 1.5 mmol) with 9-(2,3,5-tri-O-acetyl-β-D-ribofuranosyl)-2,6-dichloro-9H-purine (0.54 g, 1.2 mmol), followed by deacylation of the purified 2',3',5'-tri-O-acetyl-2-chloro-N-[(R)-1-(5-chloro-2-benzothiazolyl)thio-2-propyl]adenosine using sodium methoxide in methanol to provide the title N-[(R)-1-(5-chloro-2-benzothiazolyl)thio-2-propyl]2-chloroadenosine (0.30 g, 46%) as a solid, mp 145° C. (following column chromatography), $^1$H NMR (DMSO-d$_6$) δ1.39 (3H, d, —CHC$\underline{H}_3$), 3.45–3.78 (4H, m, H-5'$_a$ and H-5'$_b$ and —CH$_2$—), 3.96 (1H, q, H-4'), 4.14 (1H, t, H-3'), 4.52 (1H, t, H-2'), 4.72 (1H, m, —CH), 5.84 (1H, d, H-1'), 7.41 (1H, dd, Ar—H), 7.94 (1H, s, Ar—H), 8.02 (1H, dd, Ar—H), 8.42 (1H, s, H-8), 8.52 (1H, d, N—H). HPLC retention time 23.58 min [gradient elution, 20–80% acetonitrile/water (containing 0.1% TFA)].

C$_{20}$H$_{20}$Cl$_2$N$_6$O$_4$S$_2$. 1.0 H$_2$O requires C, 42.8; H, 3.9; N, 15.0. Found: C, 42.9; H, 3.8; N, 14.8%.

EXAMPLE 23

2-Chloro-N-[(R)-1-(2-thienyl)thio-2-propyl]adenosine

The title compound was prepared according to method A as described in Example 1 by reacting 2-[(R)-2-amino-1-propylthio]thiophene hydrochloride [prepared by a Mitsunobu reaction as described in Example 1 using 2-[(R)-N-tert-butyloxycarbonyl]amino-1-propanol (7.53 g, 43 mmol) and 2-mercaptothiophene (5.00 g, 43 mmol) followed by acidic hydrolysis] (0.63 g, 3.0 mmol) with 9-(2,3,5-tri-O-acetyl-β-D-ribofuranosyl)-2,6-dichloro-9H-purine (1.12 g, 2.5 mmol), followed by deacylation of the purified 2',3',5'-tri-O-acetyl-2-chloro-N-[(R)-1-(2-thienyl)thio-2-propyl]adenosine using sodium methoxide in methanol to provide the title 2-chloro-N-[(R)-1-(2-thienyl)thio-2-propyl]adenosine (0.95 g, 82%) as a foam after column chromatography. $^1$H NMR (DMSO-d$_6$) δ1.26 (3H, d, —CHC$\underline{H}_3$), 2.95–3.18 (2H, ABX, —CH$_2$—S—), 3.55 and 3.61 (2H, ABX, H-5'$_a$ and H-5'$_b$), 3.95 (1H, q, H-4), 4.14 (1H, t, H-3'), 4.44 (1H, m, —C$\underline{H}$—CH$_3$), 4.54 (1H, t, H-2'), 5.84 (1H, d, H-1'), 7.03 (1H, t, Ar—H), 7.23, 7.61 (2H, 2d, Ar—H), 8.38 (1H, d, —NH), 8.42 (1H, s, H-2). HPLC retention time 19.5 min [gradient elution, 20–80% acetonitrile/water (containing 0.1% TFA)].

C$_{17}$H$_{20}$ClN$_5$O$_4$S$_2$ requires C, 44.6; H, 4.4; N, 15.3. Found: C, 44.2; H, 4.5; N, 15.0%.

EXAMPLE 24

2-Chloro-N-[(R)-1-(4-methyl-1,2,4-triazol-3-yl)thio-2-propyl]adenosine

The title compound was prepared according to method A as described in Example 1 by reacting 3-[(R)-2-amino-1-propylthio]-4-methyl-1,2,4-triazole hydrochloride [prepared by a Mitsunobu reaction as described in Example 1 using 2-[(R)-N-tert-butyloxycarbonyl]amino-1-propanol (3.5 g, 20 mmol) and 3-mercapto-4-methyl-1,2,4-triazole (2.3 g, 20 mmol) followed by acidic hydrolysis] (0.56 g, 2.2 mmol) with 9-(2,3,5-tri-O-acetyl-β-D-ribofuranosyl)-2,6-dichloro-9H-purine (1.0 g, 2.2 mmol), followed by deacylation of the purified 2',3',5'-tri-O-acetyl-2-chloro-N-[(R)- 1-(4-methyl-1,2,4-triazol-3-yl)thio-2-propyl]adenosine using sodium methoxide in methanol to provide the title 2-chloro-N-[(R)-1-(4-methyl-1,2,4-triazol-3-yl)thio-2-propyl]adenosine (0.17 g, 17%) as a foam after column chromatography. $^1$H NMR (DMSO-d$_6$) δ1.24 (3H, d, —CHC$\underline{H}_3$), 3.56, 3.67 (2H, ABX, 5'$_a$ and H-5'$_b$), 3.95 (1H, q, H-4), 4.14 (1H, br q, H-3'), 4.15–4.42 (2H, m, —CH$_2$S—), 4.52 (1H, br q, H-2'), 4.80 (1H, m, —C$\underline{H}$CH$_3$), 5.07 (1H, br, 5'-OH), 5.22, 5.50 (2H, 2 br, 2'- and 3'-OH), 5.82 (1H, d, H-1'), 8.33 (1H, d, —NH), 8.39, 8.41 (2H, 2s, H-2 and Ar—H). HPLC retention time 7.79 min [gradient elution, 20–80% acetonitrile/water (containing 0.1% TFA)].

EXAMPLE 25

N-[(R)-1-(2-Benzimidazolyl)thio-2-propyl]-2-chloroadenosine

The title compound was prepared according to method A as described in Example 1 by reacting 2-[(R)-2-amino-1-propylthio]benzimidazole hydrochloride [prepared by a Mitsunobu reaction as described in Example 1 using 2-[(R)-N-tert-butyloxycarbonyl]amino-1-propanol (1.75 g, 10 mmol) and 2-mercaptobenzimidazole (1.5 g, 10 mmol) followed by acidic hydrolysis] (0.63 g, 2.20 mmol) with 9-(2,3,5-tri-O-acetyl-β-D-ribofuranosyl)-2,6-dichloro-9H-purine (1.0 g, 2.2 mmol), followed by deacylation of the purified 2',3',5'-tri-O-acetyl-N-[(R)-1-(2-benzimidazolyl)thio-2-propyl]-2-chloroadenosine in methanolic ammonia (200 ml) (previously saturated at −10° C.) to provide the title N-[(R)-1-(2-benzimidazolyl)thio-2-propyl]-2-chloroadenosine (0.52 g, 51%) mp 213°–215° C. after column chromatography and trituration with dichloromethane; $^1$H NMR (DMSO-d$_6$) δ1.38 (3H, d, —CHC$\underline{H}_3$), 3.95 (1H, q, H-4), 4.12 (1H, br q, H-3'), 4.42–4.70 (2H, m, —C$\underline{H}$CH$_3$ and H-2'), 5.07 (1H, br, 5'-OH), 5.22, 5.50 (2H, 2 br, 2'-and 3'-OH), 5.82 (1H, d, H-1'), 7.04–7.57 (4H, 2m, Ar—H) 8.42 (1H, s, H-2), 8.73 (1H, d, —NH). HPLC retention time 13.7 min [gradient elution, 20–80% acetonitrile/water (containing 0.1% TFA)].

EXAMPLE 26

2-Chloro-N-[(R)-1-(4-phenyl-2-thiazolyl)thio-2-propyl]adenosine

The title compound was prepared according to method A as described in Example 1 by reacting 2-[(R)-2-amino-1-propylthio]-4-phenylthiazole hydrochloride [prepared by a Mitsunobu reaction as described in Example 1 using 2-[(R)-N-tert-butyloxycarbonyl]amino-1-propanol (2.72 g, 15.5 mmol) and 2-mercapto-4-phenylthiazole (3.0 g, 15.5 mmol) followed by acidic hydrolysis] (1.15 g, 4.0 mmol) with 9-(2,3,5-tri-O-acetyl-β-D-ribofuranosyl)-2,6-dichloro-9H-purine (1.5 g, 3.35 mmol), followed by deacylation of the purified 2',3',5'-tri-O-acetyl-2-chloro-N-[(R)-1-(4-phenyl-2-thiazolyl)thio-2-propyl]adenosine using sodium methoxide in methanol to provide the title 2-chloro-N-[(R)-1-(4-phenyl- 2-thiazolyl)thio-2-propyl]adenosine (0.36 g, 20%) as a foam after column chromatography. $^1$H NMR (DMSO-d$_6$) δ1.37 (3H, d, —CHC$\underline{H}_3$), 3.4–3.73 (2H, m, 5'$_a$ and H-5'$_b$ and —CH$_2$—S—), 3.94 (1H, q, H-4), 4.13 (1H, q, H-3'), 4.52 (1H, q, H-2'), 4.71 (1H, m, —C$\underline{H}$CH$_3$), 5.06 (1H, t, 5'-OH), 5.22, 5.50 (2H, 2d, 2'- and 3'-OH), 5.83 (1H, d, H-1'), 7.33, 7.42 (3H, dt, Ar—H), 7.91 (2H, d, Ar—H), 8.41 (1H, s, H-2), 8.47 (1H, d, —NH). HPLC retention time 18.99 min [gradient elution, 20–80% acetonitrile/water (containing 0.1% TFA)].

EXAMPLE 27

2-Chloro-N-{(R)-1-[5-phenyl-(1,2,4-triazol-3-yl)]thio-2-propyl}adenosine

The title compound was prepared according to method A as described in Example 1 by reacting 3-[(R)-2-amino-1-propylthio]-5-phenyl-1,2,4-triazole hydrochloride [prepared by a Mitsunobu reaction as described in Example 1 using 2-[(R)-N-tert-butyloxycarbonyl]amino-1-propanol (2.0 g, 11.4 mmol) and 3-mercapto-5-phenyl-1,2,4-triazole (2.0 g, 11 mmol) followed by acidic hydrolysis] (0.50 g, 1.8 mmol) with 9-(2,3,5-tri-O-acetyl-β-D-ribofuranosyl)-2,6-dichloro-9H-purine (0.75 g, 1.7 mmol), followed by deacylation of the purified 2',3',5'-tri-O-acetyl-2-chloro-N-{(R)-1-[5-phenyl-(1,2,4-triazol-3-yl)]thio-2-propyl}adenosine using sodium methoxide in methanol to provide the title 2-chloro-N-{(R)-1-[5-phenyl-(1,2,4-triazol-3-yl)]thio-2-propyl}adenosine (0.21 g, 24%) as a foam after column chromatography. $^1$H NMR (DMSO-d$_6$) δ1.34 (3H, d, —CHC$\underline{H}_3$), 3.37–3.70 (4H, m, —CH$_2$—, H-5'$_a$ and H-5'$_b$), 3.95 (1H, q, H-4), 4.13 (1H, t, H-3'), 4.53 (1H, t, H-2'), 4.59–4.69 (1H, m, —C$\underline{H}$CH$_3$), 5.07 (1H, t, 5'-OH), 5.22, 5.50 (2H, 2d, 2'-and 3'-OH), 5.83 (1H, d, H-1'), 7.43–7.54 (3H, m, Ar—H), 7.90, 8.0 (2H, m, Ar—H), 8.40 (1H, s, H-2). 8.42 (1H, d, —NH), HPLC retention time 14.5 min [gradient elution, 20–80% acetonitrile/water (containing 0.1% TFA)].

C$_{21}$H$_{23}$ClN$_8$O$_4$S. 1.0 H$_2$O.0.15 C$_7$H$_{16}$ requires C, 48.0; H, 5.0; N, 20.3. Found: C, 48.2; H, 4.8; N, 20.2%.

EXAMPLE 28

N-[(R)-2-(2-Benzothiazolylthio)-1-ethyl]-2-chloroadenosine 2-(2-Benzothiazolylthio)ethylamine dihydrochloride was prepared by standard synthetic steps with a by Mitsunobu reaction between N-(2-hydroxyethyl)phthalimide and 2-mercaptobenzothiazole, followed by reaction with hydrazine hydrate. This amine dihydrochloride (0.52 g, 2.11 mmol) was reacted with 9-(2,3,5-tri-O-acetyl-β-D-ribofuranosyl)-2,6-dichloro-9H-purine (0.79 g, 1.7 mmol), followed by deacylation of the purified 2',3',5'-tri-O-acetyl-N-[(R)-2(2-benzothiazolylthio)-1-ethyl]-2-chloroadenosine using sodium methoxide in methanol to provide the title N-[(R)-2-(2-benzothiazolylthio)-1-ethyl]-2-chloroadenosine as a foam after column chromatography, $^1$H NMR (DMSO-D$_6$) δ3.54–3.60 and 3.64–3.71 (4H, m, H-5'$_a$ and H-5'$_b$ and —CH$_2$—), 3.42, (2H, q, —CH$_2$—), 3.96 (1H, d, H-4'), 4.15 (1H, q, H-3'), 4.52 (1H, q, H-2'), 5.08 (1H, t, 5'-OH), 5.22, 5.51 (2H, 2d, 2'- and 3'-OH), 5.85 (1H, d, H-1'), 7.38, 7.48 (2H, 2t, Ar—H), 7.85, 8.02 (2H, 2d, Ar—H), 8.43 (1H, s, H-8), 8.68 (1H, t, N—H). HPLC retention time 18.5 min [gradient elution, 20–80% acetonitrile/water (containing 0.1% TFA)].

EXAMPLE 29

N-[(R)-1-(2-Benzothiazolyl)amino-2-propyl]-2-chloroadenosine

2-[(R)-N-tert-butyloxycarbonylamino]-1-propylamine was prepared by standard synthetic steps from (R)-2-(N-tert-butyloxycarbonylamino)-1-propanol by Mitsunobu reaction with phthalimide followed by reaction with hydrazine hydrate. This amine (0.52 g, 3.0 mmol) and 2-chlorobenzothiazole (0.76 g, 4.5 mmol) were dissolved in dioxan (20 ml) and triethylamine (0.83 ml, 6.0 mmol) was introduced. The reaction mixture was heated at 50° C. for 18 h, evaporated and purified by "flash" column chromatography, eluting with heptane/ethyl acetate (10:3) to provide the 2-[(R)-2-(N-tert-butyloxycarbonylamino)-1-propylamino]benzothiazole (0.09 g, 10%) as an oil, TLC R$_f$ 0.31 [SiO$_2$; hexane/ethyl acetate (10:3)].

2-[(R)-(2-Amino-1-propyl)amino]benzothiazole trihydrochloride (0.065 g, (70%), m.p. 226°–226° C., was subsequently obtained by hydrolysis in a mixture of 6N hydrochloric acid and ethyl acetate (2 ml), the procedure described in Example 1. This 2-[(R)-(2-amino-1-propyl)amino]-benzothiazole trihydrochloride (0.06 g, 0.19 mmol) was reacted with 9-(2,3,5-tri-O-acetyl-β-D-ribofuranosyl)-2,6-di-chloro-9H-purine (0.127 g, 1.2 mmol), followed by deacylation of the purified 2',3',5'-tri-O-acetyl-N-[(R)-1-(2-benzothiazolyl)amino-2-propyl]-2-chloroadenosine using sodium methoxide in methanol (to remove the 2' and 3'-acetyl groups) followed by ethylamine in ethanol, which provided the title N-[(R)-1-(2-benzothiazolyl)amino-2-propyl]-2-chloroadenosine (0.027 g, 29%) as a foam (following column chromatography), $^1$H NMR (DMSO-$d_6$) δ1.25 (3H, d, —CHC$\underline{H}_3$), 3.52–3.70 (4H, m, H-5'$_a$,H-5'$_b$ and —CH$_2$—), 3.94 (1H, q, H-4'), 4.12 (1H, q, H-3'), 4.52 (1H, q, H-2'), 4.53–4.62 (1H, m, —C$\underline{H}$CH$_3$), 5.07 (1H, t, 5'-OH), 5.22, 5.48 (2H, 2d, 2'- and 3'-OH), 5.84 (1H, d, H-1'), 7.01, 7.22 (2H, 2t, Ar—H), 7.43, 7.66 (2H, 2d, Ar—H), 8.14 (1H, t, N—H), 8.41 (1H, s, H-8), 8.44 (1H, d, N—H). HPLC retention time 10.7 min [gradient elution, 20–80% acetonitrile/water (containing 0.1% TFA)].

EXAMPLE 30

N-[(R)-1-(2-Benzothiazolylsulphonyl)-2-propyl]-2-chloroadenosine

2-[(R)-2-(N-tert-Butyloxycarbonylamino)-1-propylsulphonyl]benzothiazole was prepared by oxidation of 2-[(R)-2-(N-tert-butyloxycarbonylamino)-1-propylthio]benzothiazole (see Example 5) (0.55 g, 1.7 mmol) with "Oxone" on a Montmorillionite support. A mixture of the sulphonyl and sulphinyl derivatives was obtained, and the 2-[(R)-2-(N-tert-butyloxycarbonylamino)-1-propylsulphonyl]benzothiazole was isolated following column chromatography. Deprotection was performed under standard conditions with hydrogen chloride in ethyl acetate. The resultant 2-[(R)-2-aminopropyl-1-propylsulphonyl]benzothiazole hydrochloride (0.088 g, 0.4 mmol) was reacted with 9-(2,3,5-tri-O-acetyl-β-D-ribofuranosyl)-2,6-dichloro-9H-purine (0.18 g, 0.4 mmol), followed by deacylation of the purified 2',3',5'-tri-O-acetyl-N-[(R)-1-(2-benzothiazolyl)sulphonyl-2-propyl]-2-chloroadenosine using sodium methoxide in methanol provided the title N-[(R)-1-(2-benzothiazolyl)sulphonyl-2-propyl]-2-chloroadenosine as a foam (following column chromatography); $^1$H NMR (DMSO-$d_6$) δ1.83 (3H, d, —CHC$\underline{H}_3$), 3.55, 3.66 (2H, ABX, H-5'$_a$ and H-5'$_b$), 3.96 (1H, q, H-4'), 4.17 (1H, q, H-3'), 4.59 (1H, q, H-2'), 5.08 (1H, t, 5'-OH), 5.24, 5.68 (2H, 2d, 2'- and 3'-OH), 5.95 (1H, d, H-1'), 7.34, 7.47 (2H, 2t, Ar—H), 7.84, 8.01 (2H, 2d, Ar—H), 8.14 (1H, t, N—H), 8.71 (1H, s, H-8). HPLC retention time 13.5 min [gradient elution, 20–80% acetonitrile/water (containing 0.1% TFA)].

EXAMPLE 31

5'-O-Acetyl-2-chloro-N-[(R)-1-(6-ethoxy-2-benzothiazolyl)thio-2-propyl]-adenosine Partial deacylation of the purified 2',3',5'-tri-O-acetyl-2-chloro-N-[(R)-1-(6-ethoxy-2-benzothiazolyl)thio-2-propyl]adenosine (described in Example 19) using sodium methoxide in methanol provided the title 5'-0-acetyl-N-[(R)-1-(6ethoxy2-benzothiazolyl)thio-2-propyl]-2-chloroadenosine (0.070 g, 18%) as a foam (following column chromatography), $^1$H NMR (DMSO-$d_6$) δ1.34–1.41 (6H, m, —CH$_2$C$\underline{H}_3$ and —CHC$\underline{H}_3$), 2.03 (3H, s, —COCH$_3$), 4.60 (1H, q, H-2'), 4.68 (1H, m, —C$\underline{H}$CH$_3$), 5.42, 5.62 (2H, 2d, 2'- and 3'-OH), 5.86 (1H, d, H-1'), 7.04 (1H, dd, Ar—H), 7.57, 7.72 (2H, 2d, Ar—H), 8.38 (1H, s, H-8), 8.52 (1H, d, N—H). HPLC retention time 25.6 min [gradient elution, 20–80% acetonitrile/water (containing 0.1% TFA)].

$C_{24}H_{27}ClN_8O_6S_2 \cdot 0.5\ H_2O \cdot 0.02\ C_7H_{14}$ requires C, 48.9; H, 5.0; N, 13.5. Found: C, 48.7; H, 4.9; N, 13.4%.

EXAMPLE 32

5'-O-Acetyl-2-chloro-N-{(R)-1-[5-phenyl-(1,2,4-triazol-3-yl)]thio-2-propyl}adenosine Partial deacylation of the purified 2',3',5'Tri-O-acetyl-2-chloro-N-{(R)-1-[5-phenyl-(1,2,4-triazol-3-yl)]thio-2-propyl}adenosine (described in Example 27) using sodium methoxide in methanol to provide the title 5'-O-acetyl-2-chloro-N-{(R)-1-[5-phenyl-(1,2,4-triazol-3yl)]thio-2-propyl}adenosine (0.035 g, 8%) as a foam after column chromatography. $^1$H NMR (DMSO-$d_6$) δ1.34 (3H, d, —CHC$\underline{H}_3$), 2.02 (3H, s, —COCH$_3$), 4.53–4.68 (2H, q, H-2'and —C$\underline{H}$CH$_3$), 5.40, 5.61 (2H, 2d, 2'- and 3'-OH), 5.86 (1H, d, H-1'), 7.38–8.01 (5H, 3m, Ar—H), 8.37 (1H, s, H-2). HPLC retention time 16.9 min [gradient elution, 20–80% acetonitrile/water (containing 0.1% TFA)].

We claim:
1. A compound of formula I

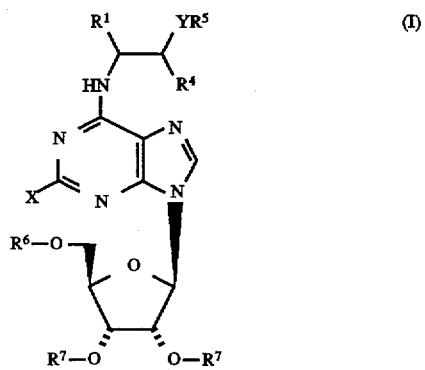

wherein

X is amino, $C_{1-6}$-alkylamino, di-$C_{1-6}$-alkylamino;

R$^1$ is H, straight or branched $C_{1-6}$-alkyl or trifluoromethyl;

R$^4$ is H or straight or branched $C_{1-6}$-alkyl; or R$^1$ and R$^4$ together form a cyclobutyl, cyclopentyl or cyclohexyl ring;

Y is O, S, SO$_2$, N—H or N-alkyl;

R$^5$ is a group of formula XII:

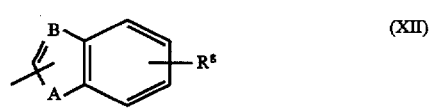

wherein A is NH, O or S; B is CH or N; and the group is substituted with R$^8$ which is H, phenyl, $C_{1-6}$-alkyl, trifluoromethyl, amino, hydroxy, $C_{1-6}$-alkoxy, cyano or halogen;

R$^6$ is hydrogen, benzoyl or $C_{1-6}$-alkanoyl and

R$^7$ is hydrogen, benzoyl or $C_{1-6}$-alkanoyl; or a pharmaceutically acceptable salt thereof.

2. A compound according to claim 1, wherein Y is S.

3. A compound according to claim 1, wherein A is S.

4. A compound according to claim 1, wherein B is N.

5. A compound according to claim 4, wherein A is S.

6. A compound according to claim 1, which is $N^6$-[(R)-1-(2-Benzothiazolyl)thio-2-propyl]-2-(dimethylamino)adenosine or a pharmaceutically acceptable salt thereof.

7. A compound according to claim 1, which is $N^6$-[(R)-1-(2-Benzothiazolyl)thio-2-propyl]-2-(ethylamino)adenosine or a pharmaceutically acceptable salt thereof.

8. A compound according to claim 1, which is 2-Amino-$N^6$-[(R)-1-(2-Benzothiazolyl)thio-2-propyl]adenosine or a pharmaceutically acceptable salt thereof.

9. A pharmaceutical composition comprising a compound according to claim 1, and a pharmaceutically acceptable carrier.

10. A pharmaceutical composition according to claim 9 in the form of an oral dosage unit containing about 1–200 mg of the active compound.

11. A method of treating myocardial ischemia, comprising administering to a person in need of such treatment an effective amount of a compound of claim 1.

12. A method of treating myocardial ischemia, comprising administering to a person in need of such treatment a pharmaceutical composition according to claim 9.

13. A method of treating cerebral ischemia, comprising administering to a person in need of such treatment an effective amount of a compound of claim 1.

14. A method of treating cerebral ischemia, comprising administering to a person in need of such treatment a pharmaceutical composition according to claim 9.

15. A compound of formula I

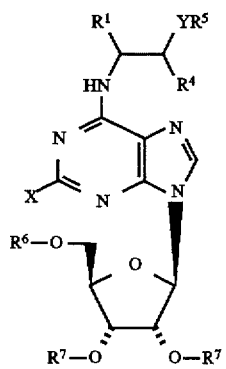

wherein

X is amino, $C_{1-6}$-alkylamino, di-$C_{1-6}$-alkylamino;

$R^1$ and $R^4$ together form a cyclobutyl, cyclopentyl or cyclohexyl ring;

Y is O, S, SO$_2$ or N-alkyl, wherein alkyl is $C_2$ or larger;

$R^5$ is a group of formula XI:

wherein A is NH, O or S; B is CH or N; C is CH or N; and the group is substituted with $R^8$ which is H, phenyl, $C_{1-6}$-alkyl, trifluoromethyl, amino, hydroxy, $C_{1-6}$-alkoxy, cyano or halogen;

$R^6$ is hydrogen, benzoyl or $C_{1-6}$-alkanoyl and $R^7$ is hydrogen, benzoyl or $C_{1-6}$-alkanoyl; or a pharmaceutically acceptable salt thereof.

16. A compound according to claim 15, wherein Y is S.
17. A compound according to claim 15, wherein A is S.
18. A compound according to claim 15, wherein B is N.
19. A compound according to claim 18, wherein A is S.

20. A pharmaceutical composition comprising a compound according to claim 15 or a pharmaceutically acceptable salt thereof and a pharmaceutically acceptable carrier.

21. A pharmaceutical composition according to claim 20 in the form of an oral dosage unit containing about 1–200 mg of the active compound.

22. A method of treating cerebral or myocardial ischemia, comprising administering to a person in need of such treatment an effective amount of a compound of claim 15.

23. A method of treating cerebral or myocardial ischemia, comprising administering to a person in need of such treatment a pharmaceutical composition according to claim 20.

24. A compound of formula I

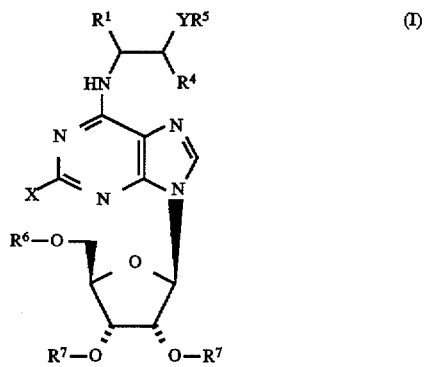

wherein

X is amino, $C_{1-6}$-alkylamino, di-$C_{1-6}$-alkylamino;

$R^1$ is H, straight or branched $C_{1-6}$-alkyl or trifluoromethyl;

$R^4$ is H or straight or branched $C_{1-6}$-alkyl;

Y is O, S, or SO$_2$;

$R^5$ is a group of formula XI:

wherein A is NH, O or S; B is CH or N; C is CH or N; and the group is substituted with $R^8$ which is H, phenyl, $C_{1-6}$-alkyl, trifluoromethyl, amino, hydroxy, $C_{1-6}$-alkoxy, cyano or halogen;

$R^6$ is hydrogen, benzoyl or $C_{1-6}$-alkanoyl and $R^7$ is hydrogen, benzoyl or $C_{1-6}$-alkanoyl; or a pharmaceutically acceptable salt thereof.

25. A compound according to claim 24, wherein Y is S.
26. A compound according to claim 24, wherein A is S.
27. A compound according to claim 24, wherein B is N.
28. A compound according to claim 27, wherein A is S.

29. A pharmaceutical composition comprising a compound according to claim 24 or a pharmaceutically acceptable salt thereof and a pharmaceutically acceptable carrier.

30. A pharmaceutical composition according to claim 29 in the form of an oral dosage unit containing about 1–200 mg of the active compound.

31. A method of treating cerebral or myocardial ischemia, comprising administering to a person in need of such treatment an effective amount of a compound of claim 24.

32. A method of treating cerebral or myocardial ischemia, comprising administering to a person in need of such treatment a pharmaceutical composition according to claim 29.

* * * * *